(12) United States Patent
Arakita et al.

(10) Patent No.: US 10,565,709 B2
(45) Date of Patent: Feb. 18, 2020

(54) IMAGE PROCESSING APPARATUS AND IMAGE PROCESSING METHOD

(71) Applicant: Canon Medical Systems Corporation, Otawara-shi (JP)

(72) Inventors: Kazumasa Arakita, Utsunomiya (JP); Masahiro Kubota, Funabashi (JP)

(73) Assignee: Canon Medical Systems Coporation, Otawara-shi (JP)

( * ) Notice: Subject to any disclaimer, the term of this patent is extended or adjusted under 35 U.S.C. 154(b) by 74 days.

(21) Appl. No.: 16/006,218

(22) Filed: Jun. 12, 2018

(65) Prior Publication Data

US 2018/0357767 A1 Dec. 13, 2018

(30) Foreign Application Priority Data

Jun. 13, 2017 (JP) ................................. 2017-116251
May 31, 2018 (JP) ................................. 2018-105280

(51) Int. Cl.
*A61B 5/00* (2006.01)
*G06T 7/00* (2017.01)
(Continued)

(52) U.S. Cl.
CPC .......... *G06T 7/0014* (2013.01); *A61B 5/0263* (2013.01); *A61B 6/032* (2013.01); *A61B 6/037* (2013.01); *A61B 6/463* (2013.01); *A61B 6/466* (2013.01); *A61B 6/503* (2013.01); *A61B 6/504* (2013.01); *A61B 6/507* (2013.01); *A61B 6/5217* (2013.01); *A61B 6/5235* (2013.01); *A61B 8/5261* (2013.01); *G06K 9/03* (2013.01); *G06K 9/46* (2013.01); *G06T 7/0012* (2013.01); *G06T 7/11* (2017.01); *G06T 7/136* (2017.01); *G06T 7/62* (2017.01); *G16H 30/20* (2018.01); *G16H 30/40* (2018.01); *G16H 40/63* (2018.01); *G16H 50/30* (2018.01); *G16H 50/50* (2018.01); *A61B 6/4417* (2013.01); *A61B 6/5247* (2013.01); *A61B 6/563* (2013.01); *A61B 8/0883* (2013.01); (Continued)

(58) Field of Classification Search
CPC ................ G06T 7/00; G06K 9/00; A61B 6/00
USPC ...................................................... 382/131
See application file for complete search history.

(56) References Cited

U.S. PATENT DOCUMENTS 8,649,584 B2 * 2/2014 Kawasaki ............ G06T 7/0014
382/128

FOREIGN PATENT DOCUMENTS

| JP | 2009-025035 | 2/2009 |
| JP | 2012-081254 | 4/2012 |
| JP | 2014-076288 | 5/2014 |

* cited by examiner

*Primary Examiner* — Abolfazl Tabatabai
(74) *Attorney, Agent, or Firm* — Oblon, McClelland, Maier & Neustady, L.L.P.

(57) ABSTRACT

An image processing apparatus according to an embodiment comprises processing circuitry configured to acquire morphology image data including a site of a subject and function image data including the site, extract a blood vessel region that corresponds to a blood vessel included in the morphology image data, calculate a fluid index in the blood vessel region, and based on the fluid index, calculate a first function index as an index indicating a function of a tissue to which a nutrient is supplied from the blood vessel, acquire a second function index as an index indicating a function of the tissue based on the function image data, detect a mismatch between the first function index and the second function index, and determine a spatial region that corresponds to the mismatch in the site.

20 Claims, 9 Drawing Sheets

(51) Int. Cl.
*G06K 9/46* (2006.01)
*G06K 9/03* (2006.01)
*A61B 6/00* (2006.01)
*A61B 5/026* (2006.01)
*A61B 8/08* (2006.01)
*G06T 7/62* (2017.01)
*A61B 6/03* (2006.01)
*G06T 7/11* (2017.01)
*G06T 7/136* (2017.01)
*G16H 30/20* (2018.01)
*G16H 50/30* (2018.01)
*G16H 30/40* (2018.01)
*G16H 50/50* (2018.01)
*G16H 40/63* (2018.01)

(52) U.S. Cl.
CPC .................. *G06K 2209/05* (2013.01); *G06T 2207/10081* (2013.01); *G06T 2207/10088* (2013.01); *G06T 2207/10104* (2013.01); *G06T 2207/10108* (2013.01); *G06T 2207/10132* (2013.01); *G06T 2207/30048* (2013.01); *G06T 2207/30101* (2013.01); *G06T 2207/30104* (2013.01)

FIG.2
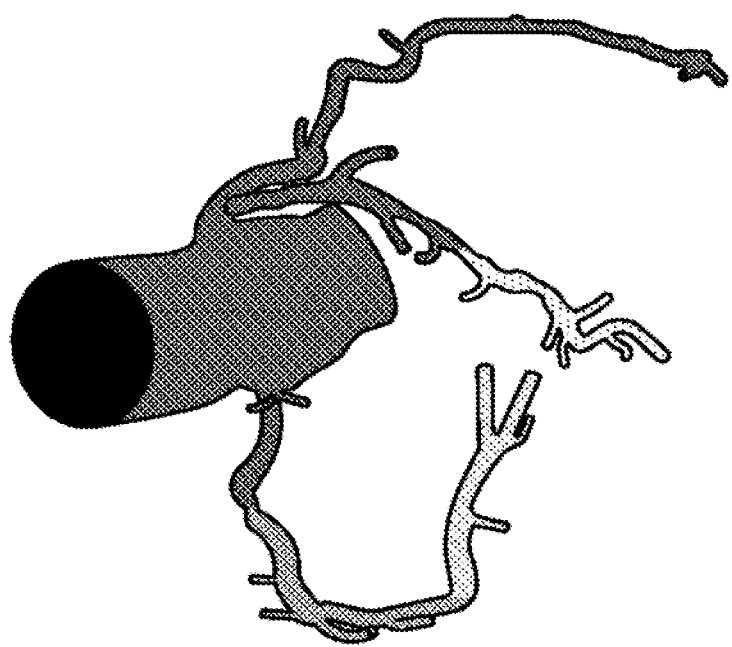
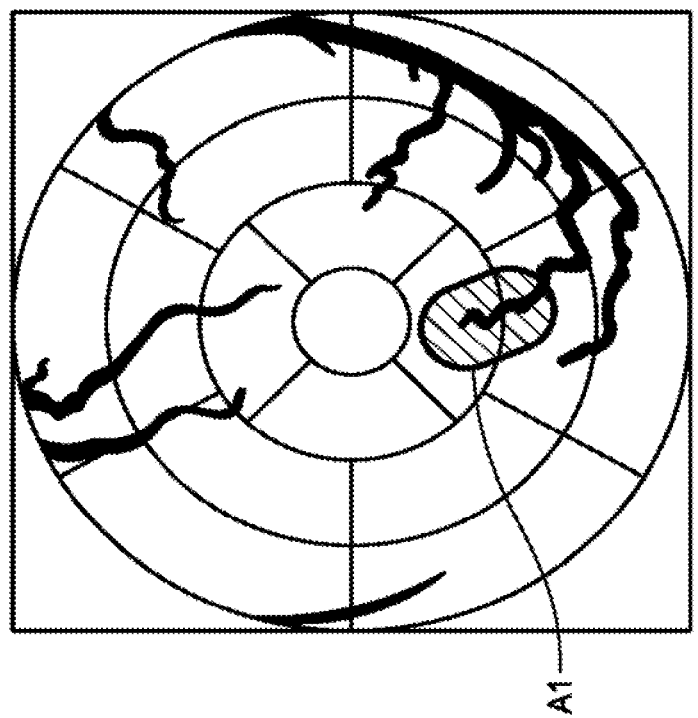
A1

FIG.3
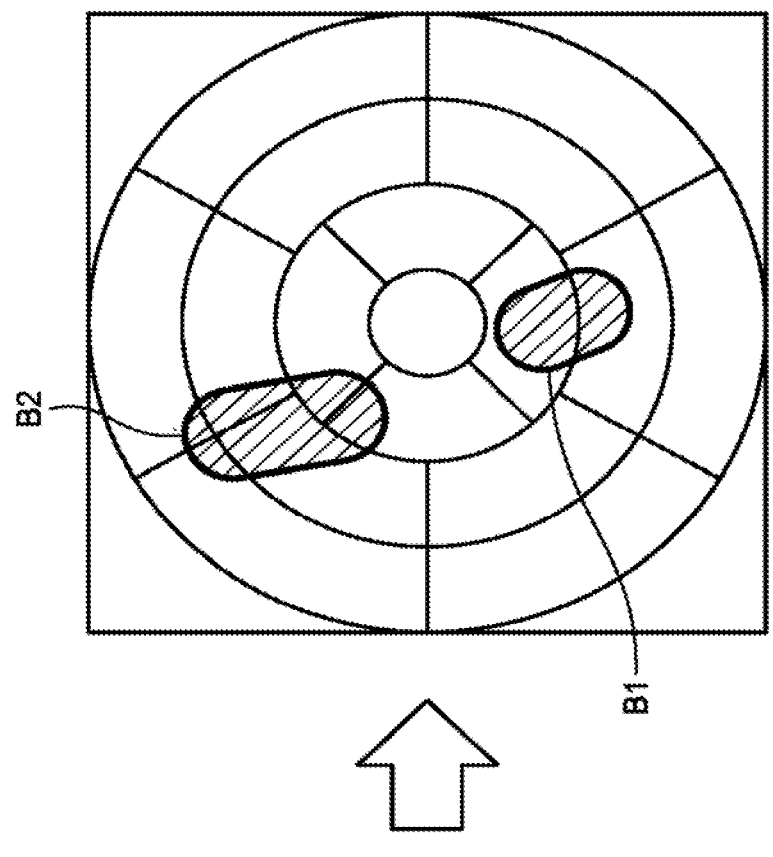
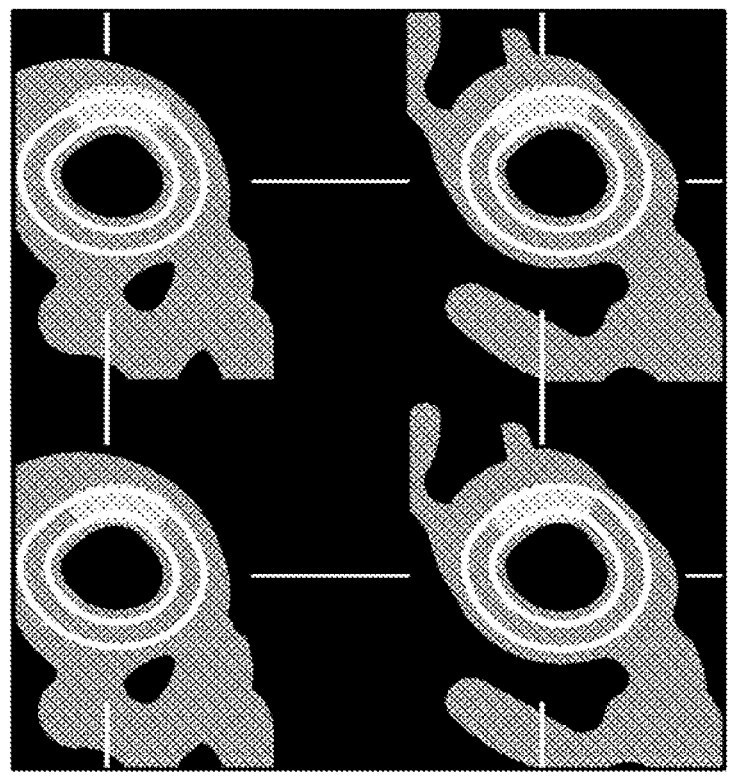

IMAGE PROCESSING APPARATUS AND IMAGE PROCESSING METHOD

CROSS-REFERENCE TO RELATED APPLICATIONS

This application is based upon and claims the benefit of priority from Japanese Patent Application No. 2017-116251, filed on Jun. 13, 2017; and Japanese Patent Application No. 2018-105280, filed on May 31, 2018, the entire contents of which are incorporated herein by reference.

FIELD

Embodiments described herein relate generally to an image processing apparatus and an image processing method.

BACKGROUND

Site information (hereafter, referred to as morphological information) obtained by analyzing morphology of a treatment target site is conventionally used to consider treatment strategies, measure treatment effects, and the like. For example, for treatment for ischemic heart diseases, morphological information such as an ischemic region in a blood vessel dominating region or a quantity of myocardium affected by ischemia, is derived from the morphology of the heart and coronary arteries, and treatment strategies are considered by using the derived morphological information. For example, doctors use morphological information to consider treatment strategies as to whether there is a need to conduct a revascularization surgery, what kind of treatment is to be provided to which blood vessel, or the like. Moreover, for example, doctors measure treatment effects on the basis of morphological information (changes in an ischemic region, ischemic myocardium quantity, or the like) before and after treatment.

This kind of morphological information is analyzed by conducting area expansion (e.g., area expansion using the Voronoi algorithm) based on the form of a coronary artery in CT image data having a contrast-enhanced blood vessel. Here, during analysis based on only the form of a coronary artery, no consideration is given to the state of myocardium, and when the form of a coronary artery is not sufficiently acquired due to limitation on the resolution of CT image data, or the like, morphological information is sometimes analyzed improperly.

BRIEF DESCRIPTION OF THE DRAWINGS

FIG. 2 is a diagram that illustrates a first index map according to the first embodiment;

FIG. 3 is a diagram that illustrates a second index map according to the first embodiment;

DETAILED DESCRIPTION

An image processing apparatus according to an embodiment comprises processing circuitry. The processing circuitry is configured to acquire morphology image data including a site of a subject and function image data including the site, extract a blood vessel region that corresponds to a blood vessel included in the morphology image data, calculate a fluid index in the blood vessel region, and based on the fluid index, calculate a first function index as an index indicating a function of a tissue to which a nutrient is supplied from the blood vessel, acquire a second function index as an index indicating a function of the tissue based on the function image data, detect a mismatch between the first function index and the second function index, and determine a spatial region that corresponds to the mismatch in the site.

With reference to drawings, a detailed explanation is given below of an embodiment of the image processing apparatus and an image processing method.

First, a first embodiment is explained. According to the first embodiment, for example an image processing system including an image processing apparatus is explained. Furthermore, according to the first embodiment, for example, an explanation is given of a case where morphological information on the heart of a subject is acquired.

Figure 1:
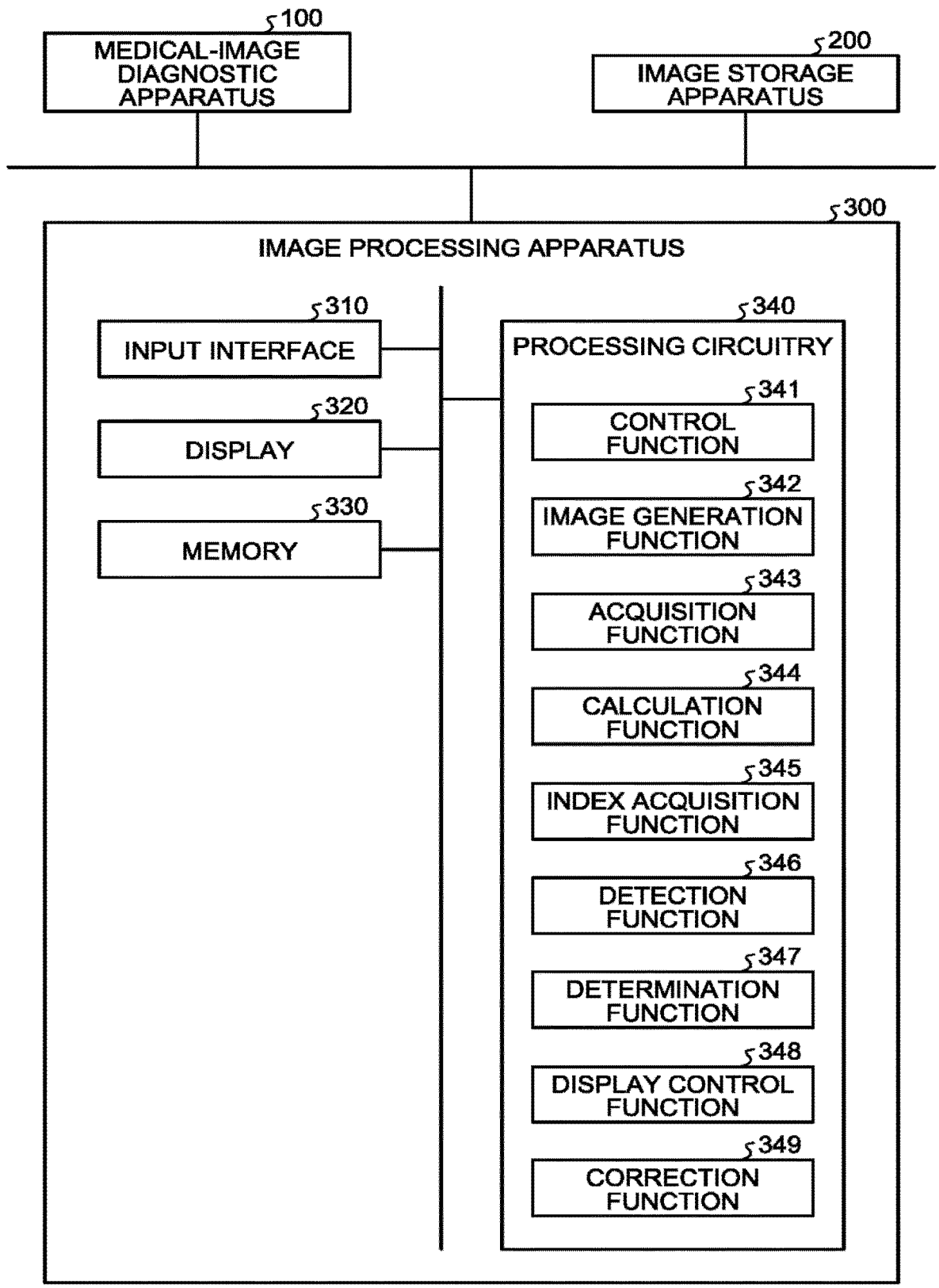
FIG. 1 is a block diagram that illustrates an example of an image processing system according to a first embodiment.

As illustrated in FIG. 1, an image processing system according to the first embodiment includes a medical-image diagnostic apparatus 100, an image storage apparatus 200, and an image processing apparatus 300. Here, FIG. 1 is a diagram that illustrates an example of the image processing system according to the first embodiment. As illustrated in FIG. 1, the medical-image diagnostic apparatus 100, the image storage apparatus 200, and the image processing apparatus 300 are connected to one another via a network.

The medical-image diagnostic apparatus 100 is an apparatus that acquires morphology image data and function image data from the subject. For example, the medical-image diagnostic apparatus 100 is an X-ray CT (computed tomography) apparatus, SPECT (single photon emission computed tomography) apparatus, PET (positron emission tomography) apparatus, a SPECT-CT apparatus that is an integration of a SPECT apparatus and an X-ray CT apparatus, a PET-CT apparatus that is an integration of a PET apparatus and an X-ray CT apparatus, an MRI (magnetic resonance imaging) apparatus, or an ultrasonic diagnostic apparatus. Among these apparatuses, one or more apparatuses acquire morphology image data and function image data as the medical-image diagnostic apparatus 100.

For example, an X-ray CT apparatus as the medical-image diagnostic apparatus 100 acquires CT image data that is morphology image data, and a SPECT apparatus as the medical-image diagnostic apparatus 100 acquires SPECT image data that is function image data. For example, a SPECT-CT apparatus as the medical-image diagnostic apparatus 100 acquires CT image data that is morphology image data and SPECT image data that is function image data. According to the present embodiment, for example, an explanation is given of a case where CT image data acquired by the X-ray CT apparatus as the medical-image diagnostic apparatus 100 is used as morphology image data and SPECT image data acquired by the SPECT apparatus as the medical-image diagnostic apparatus 100 is used as function image data.

Here, morphology image data is image data including the information on morphology of the heart of the subject. For example, CT image data is morphology image data including morphological information on structures (outlines of each ventricle, or the like) of the heart and coronary arteries of the subject. Other examples of the morphology image data include MR (magnetic resonance) image data and CT image data representing fluid indexes of blood vessel regions. Here, the fluid indexes are indexes regarding blood currents. For example, the fluid indexes are values obtained by fluid analysis on a blood vessel region in CT image data, and they include FFR (fractional flow reserve), the pressure in a blood vessel region, the flow rate of blood, the flow velocity of blood, a vector, a shear stress, or the like.

For example, an X-ray CT apparatus rotates and moves an X-ray tube and an X-ray detector with the subject at substantially the center and detects X-rays transmitted through the subject to acquire projection data. Then, the X-ray CT apparatus generates CT image data (volume data) on the basis of the acquired projection data. Then, the X-ray CT apparatus stores the generated CT image data in the image storage apparatus 200.

Furthermore, the function image data is image data including information on a function of the heart of the subject. For example, SPECT image data is function image data including physiological information on the heart of the subject, such as the state of a blood current in the heart of the subject. Other examples of the function image data include PET (positron emission computed tomography) image data, CT perfusion image data, MR perfusion image data, image data representing a result of heart function analysis on CT image data, image data representing a result of heart function analysis on MR image data, or image data representing a result of heart function analysis on ultrasound image data.

For example, the SPECT apparatus detects radiations (gamma rays) emitted from a radioactive medicine that is administered to the subject and selectively taken by a living tissue of the subject and performs correction processing such as offset correction or sensitivity correction on each detected signal to acquire SPECT projection data. Then, the SPECT apparatus performs back projection processing on SPECT projection data (e.g., projection data for which body motions have been corrected in 360 degrees), thereby reconstructing SPECT image data (volume data). Then, the SPECT apparatus stores the reconstructed SPECT image data in the image storage apparatus 200.

The image storage apparatus 200 stores image data acquired by the medical-image diagnostic apparatus 100. For example, the image storage apparatus 200 is implemented by using a computer device such as a server. According to the present embodiment, the image storage apparatus 200 acquires CT image data and SPECT image data from the medical-image diagnostic apparatus 100 via a network and stores the acquired CT image data and SPECT image data in a memory provided inside or outside the apparatus.

The image processing apparatus 300 acquires CT image data and SPECT image data via a network and performs various processes by using the acquired CT image data and SPECT image data. For example, the image processing apparatus 300 is implemented by using a computer device such as workstation. According to the present embodiment, the image processing apparatus 300 acquires CT image data and SPECT image data from the medical-image diagnostic apparatus 100 or the image storage apparatus 200 via a network. Furthermore, the image processing apparatus 300 improves the accuracy of morphological information about the heart of the subject on the basis of acquired CT image data and SPECT image data. This point is described later.

As illustrated in FIG. 1, the image processing apparatus 300 includes an input interface 310, a display 320, a memory 330, and processing circuitry 340.

The input interface 310 includes a mouse, keyboard, trackball, switch, button, joystick, touch panel, or the like, used by an operator to input various commands or various settings, and it transfers information on commands or settings received from an operator to the processing circuitry 340.

The display 320 is a monitor viewed by an operator and, under the control of the processing circuitry 340, displays various medical images to the operator or displays a GUI (graphical user interface) for receiving various commands, various settings, or the like, from the operator via the input interface 310.

The memory 330 is for example a semiconductor memory device such as a flash memory or a non-volatile storage device such as a hard disk or an optical disk. For example, the memory 330 stores CT image data and SPECT image data acquired from the medical-image diagnostic apparatus 100 or the image storage apparatus 200.

The processing circuitry 340 executes a control function 341, an image generation function 342, an acquisition function 343, a calculation function 344, an index acquisition function 345, a detection function 346, an determination function 347, a display control function 348, and a correction function 349, thereby controlling the overall operation of the image processing apparatus 300. For example, the processing circuitry 340 reads a program that corresponds to the control function 341 from the memory 330 and executes it, thereby receiving various commands and settings from the operator via the input interface 310. For example, the processing circuitry 340 reads a program that corresponds to the acquisition function 343 from the memory 330 and executes it, thereby acquiring CT image data and SPECT image data. For example, the processing circuitry 340 reads programs that correspond to the image generation function 342, the calculation function 344, the index acquisition function 345, the detection function 346, and the determination function 347 from the memory 330 and executes them so as to detect a mismatch between a function index based on CT image data and a function index based on SPECT image data and determine a spatial region that corresponds to the mismatch. This point is described later.

In the image processing apparatus 300 illustrated in FIG. 1, each processing function is stored in the memory 330 in the form of program executable by a computer. The processing circuitry 340 is a processor that implements a function that corresponds to each program by reading and executing a program from the memory 330. In other words, after reading each program, the processing circuitry 340 has a function that corresponds to the read program.

In the explanation of FIG. 1, the control function 341, the image generation function 342, the acquisition function 343, the calculation function 344, the index acquisition function 345, the detection function 346, the determination function 347, the display control function 348, and the correction function 349 are implemented by the single processing circuitry 340; however, the processing circuitry 340 may be configured by combining multiple independent processors, and each processor may execute a program to implement a function.

The term "processor" used in the above explanation means, for example, a CPU (central processing unit), a GPU (graphics processing unit), or a circuit, such as an application specific integrated circuit (ASIC), a programmable logic device (e.g., a simple programmable logic device (SPLD), a complex programmable logic device (CPLD), or a field programmable gate array (FPGA)). The processor reads a program stored in the memory 330 and executes it, thereby implementing a function. Instead of storing programs in the memory 330, a configuration may be such that programs are directly installed in a circuit of a processor. In this case, the processor reads the program installed in the circuit and executes it, thereby implementing a function. Furthermore, with regard to each processor according to the present embodiment, each processor is not always configured as a single circuit but also configured as a single processor by combining multiple independent circuits so that its function is implemented. Moreover, components in FIG. 1 may be integrated into a single processor to implement its function.

Heretofore, the configuration of the image processing system is explained. With this configuration, the image processing apparatus 300 in the image processing system improves the accuracy of morphological information. Specifically, during a process of the processing circuitry 340 described below in detail, the image processing apparatus 300 detects a mismatch in a function index of the myocardium between morphology image data and function image data and improves the accuracy of morphological information in accordance with the detected mismatch. A detailed explanation is given below of a process performed by the image processing apparatus 300 according to the first embodiment.

First, the acquisition function 343 acquires CT image data and SPECT image data from the medical-image diagnostic apparatus 100 or the image storage apparatus 200. Here, each of CT image data and SPECT image data is volume data acquired with regard to the heart of a subject. Here, CT image data and SPECT image data are acquired in any order.

Then, the calculation function 344 and the index acquisition function 345 acquire a function index indicating a function at each position of the heart of the subject. For example, the calculation function 344 and the index acquisition function 345 calculate a function index directly or indirectly representing the presence or absence of and the extent of ischemia with regard to each position of the heart from each of CT image data and SPECT image data. Hereafter, a function index based on CT image data is also referred to as a first function index. Furthermore, hereafter, a function index based on SPECT image data is also referred to as a second function index.

For example, the calculation function 344 conducts fluid analysis on CT image data and calculates the first function index on the basis of a blood vessel region in the CT image data and an analysis result. For example, the calculation function 344 conducts fluid analysis to calculate a fluid index in a blood vessel region and calculates the first function index on the basis of the fluid index. Here, for example, the fluid index is a value obtained by fluid analysis on a blood vessel region, and it includes FFR, the pressure in a blood vessel region, the flow rate of blood, the flow velocity of blood, a vector, shear stress, or the like. An explanation is given below by using FFR as an example of the fluid index. Furthermore, hereafter, fluid analysis for calculating FFR is also referred to as FFR analysis. Furthermore, the image generation function 342 generates a first index map by projecting the first function index onto a plane. This point is described below in detail.

First, the calculation function 344 extracts a blood vessel region that corresponds to a blood vessel included in CT image data acquired by the acquisition function 343. For example, the calculation function 344 compares a pixel value (CT value, or the like) with a threshold on a pixel by pixel basis, thereby extracting a blood vessel region from CT image data. For example, when the pixel value of a blood vessel represented in CT image data is small (dark), the calculation function 344 extracts a pixel with a pixel value smaller than the threshold as a blood vessel region. The threshold may be a preset value, and it may be a value set by an operator. Furthermore, there may be a case where, instead of extracting a blood vessel region by the calculation function 344, the acquisition function 343 acquires CT image data in which a blood vessel region has been already extracted.

Then, the calculation function 344 conducts fluid analysis by using CT image data to calculate FFR. Here, the FFR is, for example, the ratio of the pressure in a proximal area of a blood vessel that is close to the aortic arc to the pressure in a distal area that is far from the aortic arc, and it is represented by "FFR=Pd (the pressure in a distal area)/Pa (the pressure in a proximal area)".

For example, the calculation function 344 first calculates the pressure at each position of a blood vessel region on the basis of blood vessel form data and setting conditions. Here, the blood vessel form data is for example the outline of the inner cavity or the outer wall of a blood vessel, the cross-sectional area or the core line of a blood vessel, and the like. The calculation function 344 may acquire blood vessel form data from a blood vessel region in CT image data. Furthermore, the setting conditions are, for example, analysis conditions such as the property value of blood, a condition of repeated calculation, or the default value of analysis. Furthermore, the calculation function 344 may calculate not only pressure but also various indexes (the flow rate of blood, the flow velocity of blood, a vector, shear stress, and the like) regarding blood currents.

Here, the calculation function 344 calculates the pressure at each position along the core line of a blood vessel and calculates the distribution of pressures in a blood vessel region. Then, the calculation function 344 calculates FFR at each position of the blood vessel region from the distribution of calculated pressures. For example, the calculation function 344 sets a proximal area in the blood vessel region at a position close to the aortic arc and divides the pressure at each position of the blood vessel region by the pressure in the proximal area, thereby calculating FFR at each position of the blood vessel region.

Next, the image generation function 342 generates volume data including the morphology information on a coronary artery and an analysis result of the FFR from the CT image data and the FFR. That is, the image generation function 342 generates CT image data representing the FFR of the blood vessel region. Hereafter, CT image data representing FFR of a blood vessel region is also referred to as FFR image data. FFR image data is for example CT image data where the color corresponding to FFR or the value of FFR is applied to each position of a blood vessel region. Furthermore, there may be a case where the acquisition function 343 acquires FFR image data instead of calculating FFR by the calculation function 344 and generating FFR image data by the image generation function 342.

The calculation function 344 is capable of extracting various types of information from FFR image data. For example, the calculation function 344 extracts core line coordinates of a blood vessel from FFR image data. The calculation function 344 may use the core line coordinates of a blood vessel acquired from CT image data for FFR analysis as the core line coordinates of a blood vessel in FFR image data. Furthermore, for example, the calculation function 344 compares FFR image data with model data (e.g., model data indicating AHA (American Heart Association) classification) indicating the shape and the name of a coronary artery, thereby extracting information (label information) that indicates the relation between each core line and the name of a coronary artery. Furthermore, for example, the calculation function 344 extracts the area of a ventricle from FFR image data. For example, an explanation is given below of a case where the calculation function 344 extracts the area of the left ventricle. For example, the calculation function 344 compares FFR image data with model data indicating the shape and the name of each ventricle and extracts the coordinates that correspond to the lining membrane of the left ventricle and the outer membrane of the left ventricle as the area of the left ventricle. Furthermore, for example, the calculation function 344 extracts the cardiac axis of the extracted left ventricle. Furthermore, for example, the calculation function 344 extracts the direction of the right ventricle based on the extracted left ventricle.

Next, the calculation function 344 calculates the first function index as an index indicating a function of the tissue to which nutrients are supplied from a blood vessel with respect to each position of the heart of the subject on the basis of FFR image data. For example, the calculation function 344 first determines a dominant blood vessel at any position (hereafter, referred to as a position P1) of the heart of the subject. For example, the calculation function 344 determines a blood vessel region with the shortest distance from the position P1 as a blood vessel region that dominates the position P1. Specifically, as the blood vessel region that dominates the position P1, the calculation function 344 determines the core line coordinates with the shortest distance from the coordinates of the position P1. Then, the calculation function 344 acquires the FFR at the determined core line coordinates as the first function index of the position P1. Furthermore, the calculation function 344 acquires the first function index with respect to each position of the heart other than the position P1 in the same manner.

Here, there may be a case where the detection function 346 acquires morphological information regarding the heart of the subject from FFR image data. For example, based on the first function index, the detection function 346 is capable of determining a region (ischemic region) of the heart where ischemia is occurring and is capable of calculating the quantity of myocardium (ischemic myocardium quantity) where ischemia is occurring. Specifically, the detection function 346 determines whether the value of FFR calculated as the first function index is equal to or less than a threshold with respect to each position of the heart and determines the set of positions where the value of FFR is equal to or less than the threshold as an ischemic region. Furthermore, the detection function 346 calculates an ischemic myocardium quantity in accordance with the ischemic region. Furthermore, there may be a case where the display control function 348 presents morphological information to an operator. For example, the display control function 348 displays a display image illustrating an ischemic region and a value of FFR on the display 320. Here, on the display image, the display control function 348 may display label information, an area of the left ventricle, the core axis of the left ventricle, the direction of the right ventricle, and the like. Moreover, for example, the display control function 348 displays an ischemic myocardium quantity on the display 320.

Next, the image generation function 342 projects the first function index at each position of the heart onto a plane, thereby generating the first index map. Here, the first index map based on FFR image data is explained with reference to FIG. 2. FIG. 2 is a diagram that illustrates the first index map according to the first embodiment. An explanation is given below of a case where, as the first index map, the image generation function 342 generates a polar map (polar coordinates display) from FFR image data representing the distribution of the first function indexes.

The left section of FIG. 2 is FFR image data representing FFR at each position of coronary arteries in colors. Here, the left section of FIG. 2 does not represent regions other than blood vessel regions. The image generation function 342 generates a polar map illustrated in the right section of FIG. 2 from the FFR image data illustrated in the left section of FIG. 2. Specifically, with regard to the lining membrane of the left ventricle extracted from FFR image data, the image generation function 342 superimposes cross-sectional surfaces perpendicular to the cardiac axis with the ventricular apex as a center, thereby generating a polar map. That is, the polar map illustrated in the right section of FIG. 2 is equivalent to a diagram of the lining membrane of the left ventricle viewed from the ventricular apex in a cardiac axis direction. Furthermore, a first function index is projected onto each position of the polar map illustrated in the right section of FIG. 2

Here, FIG. 2 illustrates a case where a first function index and a blood vessel region are projected onto each position of the polar map; however, this is not a limitation on embodiments. For example, as the first index map, the image generation function 342 may generate a polar map where only the first function indexes are projected. Furthermore, for example, as the first index map, the image generation function 342 may generate a polar map that indicates a blood vessel dominating region in addition to the distribution of the first function indexes. For example, the image generation function 342 classifies a blood vessel dominating region of the right coronary artery (RCA), a blood vessel dominating region of the left anterior descending (LAD), and a blood vessel dominating region of the left circumflex (LCX), thereby generating a polar map that is color-coded or attached with a border line.

Next, the detection function 346 determines the position of an ischemic region on the first index map. For example, the detection function 346 determines whether the first function index (the value of FFR) is equal to or less than the threshold at each position of the polar map illustrated in the right section of FIG. 2, and determines the set of positions where the value of FFR is equal to or less than the threshold as an ischemic region. For example, the detection function 346 determines a region A1 illustrated in the right section of FIG. 2 as an ischemic region.

An explanation is given above of a case where FFR is acquired as the first function index, the FFR is projected on a polar map, and it is determined whether each position of the polar map is an ischemic region in accordance with the FFR; however, this is not a limitation on embodiments. For example, there may be a case where it is determined whether each position of FFR image data is an ischemic region on the basis of FFR, a determination result is acquired as the first function index, the determination result is projected onto a polar map, and it is determined whether each position of the polar map is an ischemic region in accordance with the determination result. In other words, the calculation function 344 may calculate FFR itself as the first function index or may calculate an index based on FFR as the first function index.

For example, the calculation function 344 first determines whether the value of FFR is equal to or less than the threshold at each position of the heart in FFR image data and determines the set of positions where the value of FFR is equal to or less than the threshold as an ischemic region. Next, the calculation function 344 calculates information (e.g., Yes/No) indicating whether each position of the heart in FFR image data is an ischemic region as the first function index. Then, the image generation function 342 projects the first function index at each position of the heart onto a plane to generate a polar map, and the detection function 346 determines an ischemic region based on the first function index at each position of the polar map. That is, the detection function 346 determines the set of positions where "Yes" is projected as the first function index in the polar map as an ischemic region.

Next, an explanation is given of the second function index and a second index map where the second function index is projected on a plane. For example, the index acquisition function 345 conducts perfusion analysis on SPECT image data and, in accordance with an analysis result, acquires the second function index as an index indicating a function of the tissue to which nutrients are supplied from a blood vessel. Furthermore, the image generation function 342 projects the second function index on a plane, thereby generating a second index map. This point is described below in detail.

The index acquisition function 345 conducts myocardium perfusion analysis by using SPECT image data acquired by the acquisition function 343. For example, the index acquisition function 345 determines blood current dynamics in a blood vessel of the heart of the subject on the basis of the magnitude of a pixel value in SPECT image data or comparison between sets of SPECT image data acquired with a time interval, and it acquires an index indicating blood current dynamics as the second function index. In other words, the index acquisition function 345 acquires the degree of accumulation of a radioactive medicine as the second function index.

For example, at the position where a blood current is normal in the heart of the subject, a radioactive medicine injected into the subject is gradually accumulated, and the detected radiation (gamma rays) is gradually increased. Therefore, the index acquisition function 345 compares multiple sets of SPECT image data and, with regard to the position where a pixel value changes largely, acquires an index indicating that the blood current is normal as the second function index. Conversely, at a position (ischemic region) where a blood current is not normal due to stenosis of a blood vessel, or the like, in the heart of the subject, a radioactive medicine is slowly accumulated as compared with a position where a blood current is normal. Therefore, the index acquisition function 345 compares multiple sets of SPECT image data and, with regard to a position where a pixel value changes slightly, acquires an index indicating that a blood current is abnormal as the second function index.

For example, the index acquisition function 345 generates a time density curve (TDC) indicating a temporal change in a pixel value, or the like, of SPECT image data with respect to each position of the heart. Then, the index acquisition function 345 acquires, as the second function index, a predetermined density value such as the maximum value or the minimum value of density in a TDC or a value of 90% of the maximum value, the tilt of a time density curve, the time elapsing until a predetermined density is reached, a mean transit time (MTT) of blood, a blood flow (cerebral blood flow (CBF)), a blood volume (a cerebral blood volume (CBV)), the value indicating a state of blood flowing into or out of a predetermined area, or the like.

Next, the image generation function 342 generates SPECT image data including a result of perfusion analysis. For example, the image generation function 342 generates volume data indicating the distribution of indexes (the second function indexes) that represent blood current dynamics in a blood vessel of the heart of the subject. Hereafter, SPECT image data including a result of perfusion analysis is referred to as perfusion image data. Furthermore, instead of generation of perfusion image data by the image generation function 342, there may be a case where the acquisition function 343 acquires perfusion image data. In this case, the index acquisition function 345 may acquire the second function index from perfusion image data.

Next, the image generation function 342 projects the second function index at each position of the heart onto a plane, thereby generating a second index map. Here, the second index map based on perfusion image data is explained with reference to FIG. 3. FIG. 3 is a diagram that illustrates the second index map according to the first embodiment. Furthermore, an explanation is given below of a case where the image generation function 342 generates a polar map (also called "bull's eye") as the second index map from perfusion image data indicating the distribution of the second function indexes.

First, the index acquisition function 345 conducts myocardium perfusion analysis by using SPECT image data to acquire the second function index with respect to each position of the heart of the subject. Then, the image generation function 342 generates perfusion image data indicating the distribution of the second function indexes. Then, the image generation function 342 generates a polar map from the perfusion image data. Specifically, with regard to the lining membrane of the left ventricle extracted from perfusion image data, the image generation function 342 generates a polar map by superimposing cross-sectional surfaces perpendicular to the cardiac axis with the ventricular apex as a center. For example, the left section of FIG. 3 illustrates four cross-sectional surfaces perpendicular to the cardiac axis, and an inner circle of the double circle on each cross-sectional surface represents the cross-sectional surface of the lining membrane of the left ventricle perpendicular to the cardiac axis. Then, the second function index is projected onto each position of the polar map illustrated in the right section of FIG. 3.

Furthermore, as illustrated in the left section of FIG. 3, the image generation function 342 is capable of determining the lining membrane (the inner circle of the double circle in the left section of FIG. 3) of the left ventricle and the outer membrane (the outer circle of the double circle in the left section of FIG. 3) in perfusion image data. Then, the image generation function 342 is capable of generating a polar map based on the determined lining membrane of the left ventricle. In this aspect, although perfusion image data, which is a function image, does not include high-accuracy morphology information on coronary arteries, positions of the lining membrane of the left ventricle, the cardiac axis, the ventricular apex, and the like, are determinable, whereby the image generation function 342 is capable of generating a polar map from perfusion image data.

Next, the detection function 346 determines an ischemic region in the second index map. For example, the detection function 346 determines whether the second function index (e.g., blood flow) is equal to or less than a threshold at each position of the polar map illustrated in the right section of FIG. 3 and determines the set of positions where a blood flow is equal to or less than the threshold as an ischemic region. For example, the detection function 346 determines a region B1 and a region B2 illustrated in the right section of FIG. 3 as ischemic regions.

An explanation is given above of a case where an index (blood flow, or the like) indicating blood current dynamics of a blood vessel in the heart is acquired as the second function index, the index indicating blood current dynamics is projected onto a polar map, and it is determined whether each position of the polar map is an ischemic region on the basis of the index indicating blood current dynamics; however, this is not a limitation on embodiments. For example, there may be a case where it is determined whether each position of perfusion image data is an ischemic region on the basis of an index indicating blood current dynamics, a determination result is acquired as the second function index, a determination result is projected onto a polar map, and it is determined whether each position of the polar map is an ischemic region in accordance with the determination result. In other words, the index acquisition function 345 may acquire an index indicating blood current dynamics as the second function index or may acquire the index based on an index indicating blood current dynamics as the second function index.

For example, the index acquisition function 345 first determines whether a blood flow is equal to or less than the threshold with regard to each position of the heart in perfusion image data and determines the set of positions where a blood flow is equal to or less than the threshold as an ischemic region. Next, as the second function index, the index acquisition function 345 acquires information (e.g., Yes/No) indicating whether each position of the heart in perfusion image data is an ischemic region. Then, the image generation function 342 projects the second function index at each position of the heart onto a plane to generate a polar map, and the detection function 346 determines an ischemic region from the second function index at each position of the polar map. Specifically, the detection function 346 determines the set of positions where "Yes" is projected as the second function index on a polar map as an ischemic region.

Figure 4:
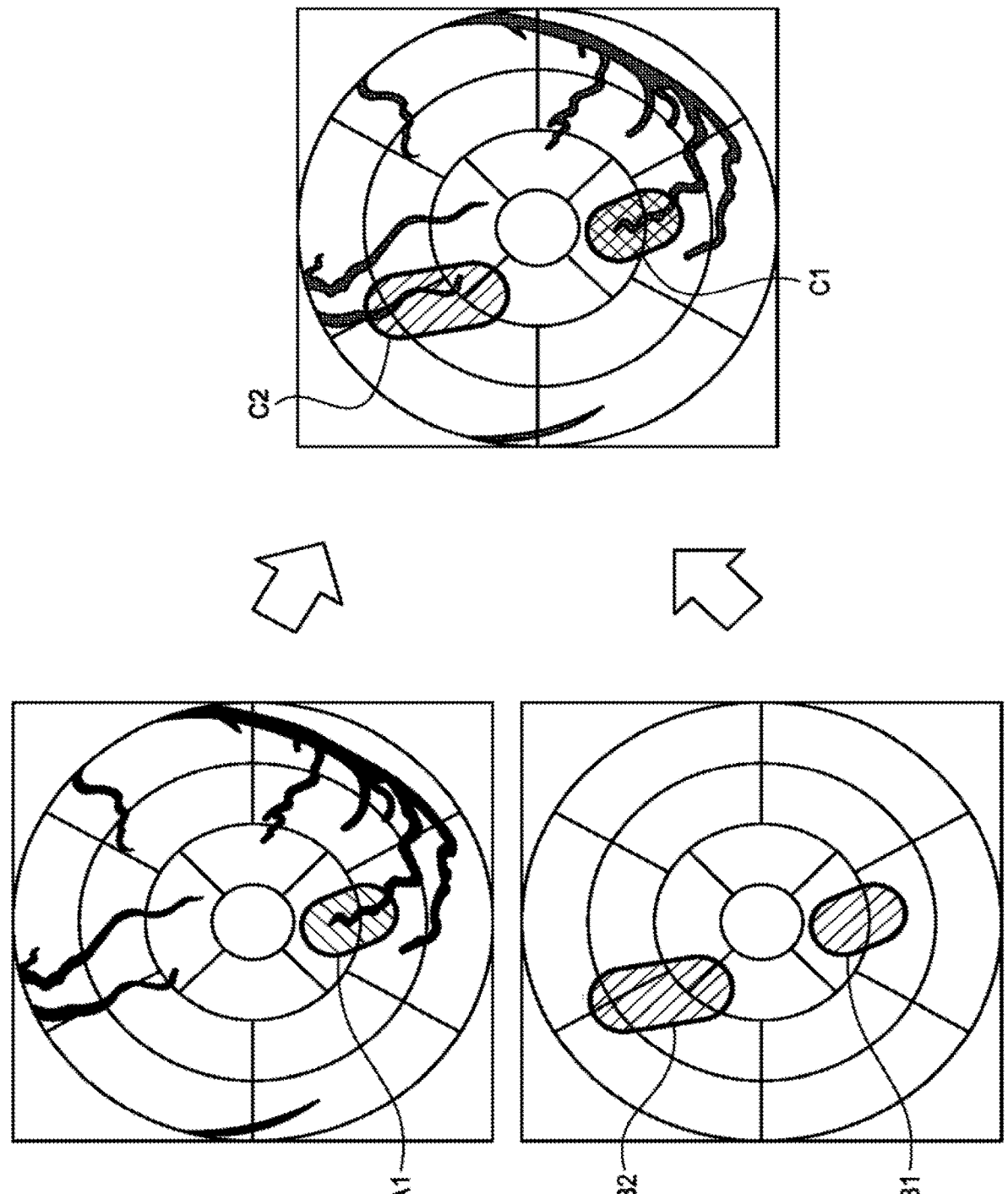
FIG. 4 is a diagram that illustrates a synthesis map according to the first embodiment.

Then, the image generation function 342 registers and synthesizes the first index map and the second index map, thereby generating a synthesis map. For example, the image generation function 342 registers the polar map illustrated in the right section of FIG. 2 and the polar map illustrated in the right section of FIG. 3, and synthesizes these polar maps after the registration, thereby generating a synthesis map. Here, the synthesis map based on the first index map and the second index map is explained with reference to FIG. 4. FIG. 4 is a diagram that illustrates a synthesis map according to the first embodiment.

The upper left section of FIG. 4 is the first index map (the polar map illustrated in the right section of FIG. 2) where a first function index is projected onto each position and the region A1 is determined as an ischemic region. The lower left section of FIG. 4 is the second index map (the polar map illustrated in the right section of FIG. 3) where a second function index is projected onto each position and the region B1 and the region B2 are determined as ischemic regions. The image generation function 342 registers and synthesizes the first index map and the second index map, thereby generating the synthesis map illustrated in the right section of FIG. 4.

Here, an example of registration between the first index map and the second index map is explained. For example, the image generation function 342 registers FFR image data and perfusion image data before the first index map and the second index map are generated. For example, the image generation function 342 extracts a feature point (landmark) from each of FFR image data and perfusion image data and registers the FFR image data and the perfusion image data such that the positions of the feature points are matched with each other. Here, feature points are structural feature points of the heart, such as a joint area (septum) between the right ventricle and the left ventricle in images. Furthermore, feature points may be extracted in accordance with an operator's designation operation. Furthermore, for example, the image generation function 342 conducts comparison by using atlas data on the heart (model data regarding the structure of the heart) to determine the left ventricle area in each of FFR image data and perfusion image data, and it registers FFR image data and perfusion image data such that the positions of the left ventricle areas are matched with each other.

In this way, by registering FFR image data and perfusion image data, the image generation function 342 matches projection conditions for generating the first index map and the second index map so as to register the first index map and the second index map. For example, with regard to the lining membrane of the left ventricle in FFR image data, the image generation function 342 first superimposes cross-sectional surfaces perpendicular to the cardiac axis with the ventricular apex as a center, thereby generating the first index map. Then, in perfusion image data, the image generation function 342 determines the positions that correspond to the lining membrane of the left ventricle, the cardiac axis, and the ventricular apex in the FFR image data and, based on the determined positions, generates the second index map. That is, the image generation function 342 conducts registration in the stage of volume data and performs projection onto a plane under the same condition, thereby registering the first index map and the second index map.

On the synthesis map illustrated in the right section of FIG. 4, the first function index and the second function index are projected onto each position. Here, the detection function 346 detects a mismatch between the first function index and the second function index from the synthesis map. For example, the detection function 346 detects, as a mismatch, a region C2 that is an ischemic region (a region B2) on the second index map and that is not an ischemic region on the first index map.

That is, a mismatch between the first function index and the second function index is a mismatch between a myocardium function evaluation based on the first function index and a myocardium function evaluation based on the second function index, and it is not limited to a simple mismatch between numerical values. For example, with regard to a region C1 of the synthesis map, although numerical values are largely different in the first function index and the second function index, the region C1 is an ischemic region on both the first index map and the second index map, and each of the function indexes indicates an identical function. Therefore, the detection function 346 does not detect the region C1 as a mismatch.

Furthermore, although an explanation is given of a case where regions that are differently determined whether they are ischemic regions are detected as a mismatch, this is not a limitation on embodiments. For example, the detection function 346 evaluates the degree of ischemia at each position of the heart as a numerical value (e.g., a numerical value from 0 to 1) based on each of the first function index and the second function index. Then, from the synthesis map, the detection function 346 is capable of detecting a region having a difference in numerical values larger than a threshold as a mismatch.

Here, the display control function 348 may display a synthesis map on the display 320. For example, if a mismatch occurs due to an artifact in image data, an operator may view a synthesis map to recognize the presence of the artifact and give a command to the acquisition function 343 so as to acquire image data again. Furthermore, for example, if a mismatch occurs due to registration between the first index map and the second index map for generating a synthesis map, substantially the entirety of a region that is an ischemic region in any of the first index map and the second index map is detected as a mismatch; therefore, when viewing a synthesis map, an operator may determine that registration is not proper and give a command to the image generation function 342 so as to conduct registration again.

Then, the determination function 347 determines the spatial region that corresponds to a mismatch in the heart of the subject. For example, in CT image data such as FFR image data, the determination function 347 determines the region that corresponds to the region C2 detected as a mismatch from the synthesis map. For example, the determination function 347 determines the region that corresponds to the region C2 on the basis of the correspondence relation between each position of the synthesis map illustrated in the right section of FIG. 4 and each position of the lining membrane of the left ventricle of the subject.

For example, the determination function 347 acquires the correspondence relation of positions used by the image generation function 342 to generate the first index map (the right section of FIG. 2) from the FFR image data (the left section of FIG. 2). That is, the determination function 347 acquires the correspondence relation between each position of the lining membrane of the left ventricle and each position of the first index map. Here, as the synthesis map is a synthesis of the first index map and the second index map, the correspondence relation between each position of the lining membrane of the left ventricle and each position of the first index map represents the correspondence relation between each position of the lining membrane of the left ventricle and each position of the synthesis map. Therefore, by using acquired correspondence relation, the determination function 347 is capable of determining the region that corresponds to the region C2 in the synthesis map, included in the lining membrane of the left ventricle of the subject.

In the same manner, in CT image data where FFR is not represented, the determination function 347 is also capable of determining the region that corresponds to the region C2. Furthermore, the determination function 347 is capable of determining the region that corresponds to the region C2 in any image data including the heart of the subject (perfusion image data, SPECT image data where a result of perfusion analysis is not represented, or the like) by registering it with CT image data, such as FFR image data, where a spatial region is determined.

Figure 5:
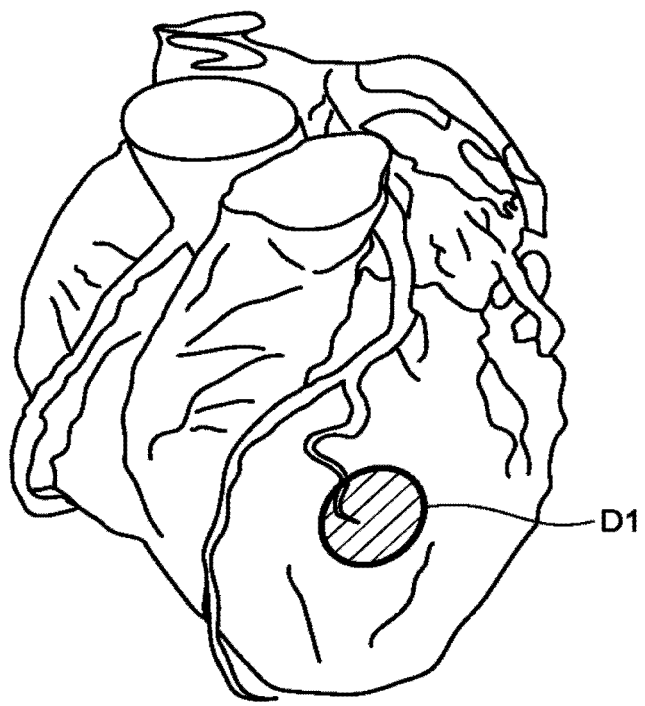
FIG. 5 is a diagram that illustrates a spatial region that corresponds to a mismatch according to the first embodiment.

Furthermore, the display control function 348 displays image data indicating a spatial region on the display 320. For example, the image generation function 342 first performs various types of image processing on CT image data, thereby generating a display image. Here, the image generation function 342 generates a display image such that an operator is capable of recognizing the spatial region determined by the determination function 347. For example, the image generation function 342 generates FFR images by representing the spatial region that corresponds to the region C2 in a color that is different from those of the other regions or by highlighting an outline. For example, as illustrated in FIG. 5, the display control function 348 indicates a spatial region D1 that corresponds to the region C2 in the display image illustrating the heart of the subject and displays it on the display 320. Here, FIG. 5 is a diagram that illustrates a spatial region that corresponds to a mismatch according to the first embodiment.

By displaying the spatial region D1 that corresponds to the region C2 on the display 320, the display control function 348 is capable of giving a warning that there is a mismatch in the spatial region D1. That is, the image generation function 342 is capable of presenting to an operator that there is a possibility that the region that is determined not to be an ischemic region by viewing only morphological information acquired from CT image data is actually an ischemic region. Then, the operator may observe the spatial region D1 in CT image data or SPECT image data to determine whether the spatial region D1 is an ischemic region, or it may determine whether CT image data or SPECT image data needs to be acquired again. Thus, by displaying image data indicating a spatial region, the display control function 348 may improve the accuracy of morphological information.

Furthermore, the correction function 349 is capable of correcting CT image data on the basis of a detected mismatch. For example, when a mismatch is detected, the correction function 349 re-extracts a blood vessel from CT image data and corrects a blood vessel region in the CT image data in accordance with the re-extracted blood vessel. Furthermore, correction of CT image data by the correction function 349 may be conducted instead of display of image data indicating a spatial region by the display control function 348 or may be conducted together with it. Correction of CT image data by the correction function 349 is explained below in detail.

First, an explanation is given of a case where a region (hereafter, also referred to as a first mismatch region) that is an ischemic region on the first index map based on CT image data and that is not an ischemic region on the second index map based on SPECT image data is detected as a mismatch. In this case, the shape of a blood vessel region in the CT image data indicates that ischemia occurs in the heart region that corresponds to the first mismatch region. Conversely, a result of perfusion analysis based on the SPECT image indicates that ischemia does not occur in the heart region that corresponds to the first mismatch region.

In this case, there is a possibility that a blood vessel is missed when a blood vessel is extracted from CT image data. That is, there is a possibility that nutrients are supplied to the heart region that corresponds to the first mismatch region by a blood vessel that is not extracted from the CT image data and in actuality ischemia does not occur. If there is a blood vessel that supplies nutrients to the heart region that corresponds to the first mismatch region, the operator may determine that it is not necessary to conduct a revascularization surgery.

Next, an explanation is given of a case where a region (hereafter, also referred to as a second mismatch region) that is an ischemic region on the second index map based on SPECT image data and that is not an ischemic region on the first index map based on CT image data is detected as a mismatch. Here, the region C2 illustrated in the right section of FIG. 4 is an example of the second mismatch region. In this case, a result of perfusion analysis based on an SPECT image indicates that ischemia occurs in the heart region that corresponds to the second mismatch region. Conversely, the shape of the blood vessel region in the CT image data indicates that ischemia does not occur in the heart region that corresponds to the second mismatch region.

In this case, there is a possibility that stenosis of a blood vessel is missed when a blood vessel is extracted from CT image data. That is, there is a possibility that FFR is reduced and ischemia occurs in the heart region that corresponds to the first mismatch region due to stenosis that is not extracted from CT image data. Furthermore, there is a possibility that a blood vessel that is not extracted from CT image data includes responsible stenosis and ischemia occurs in the heart region that corresponds to the first mismatch region. If ischemia occurs in the heart region that corresponds to the first mismatch region, an operator may determine that it is desirable to conduct a revascularization surgery.

Therefore, the correction function 349 changes an extraction parameter for a blood vessel region and re-extracts a blood vessel from CT image data, thereby searching for a blood vessel or stenosis that causes the first mismatch region or the second mismatch region. For example, the correction function 349 uses an extraction parameter different from the extraction parameter used by the calculation function 344 to extract a blood vessel region from CT image data, thereby re-extracting a blood vessel. Here, the extraction parameter is, for example, the position of a seed point or the pixel value that is a reference for extraction.

An explanation is given below of a case where, for example, each pixel of CT image data has tone of "1024". First, to extract a blood vessel region from CT image data, the calculation function 344 sets the position of a seed point as a "proximal area" and sets "300" as a threshold, thereby extracting a blood vessel. Specifically, the calculation function 344 sets the position closer to the aortic arc in the left ventricle in CT image data as a proximal area, sequentially retrieves pixels included in the CT image data by using one or more points included in the proximal area as seed points, and extracts pixels having a pixel value smaller than "300" as a blood vessel.

Then, after the detection function 346 detects a mismatch and the determination function 347 determines a spatial region, the correction function 349 sets the position of a seed point as the "region that corresponds to the mismatch" and sets "150" as a threshold, thereby re-extracting a blood vessel. That is, in CT image data, the correction function 349 sequentially retrieves pixels included in the CT image data by using one or more points included in the region that corresponds to a mismatch as seed points and re-extracts pixels having a pixel value smaller than "150" as a blood vessel. Then, the correction function 349 corrects a blood vessel region in the CT image data in accordance with the re-extracted blood vessel. For example, the correction function 349 adds a blood vessel region or corrects the shape of a blood vessel region in accordance with a result of re-extraction.

By changing the position of a seed point from the "proximal area" to the "region that corresponds to a mismatch", the manner of applying a blood vessel extraction algorithm is changed so that a blood vessel or stenosis that is not previously detected may be newly extracted in some cases. For example, when the position of a seed point is the "proximal area", pixels that correspond to a blood vessel are sequentially extracted from upstream by using the "proximal area" as a starting point. On the other hand, when the position of a seed point is "the region that corresponds to a mismatch", pixels that correspond to a blood vessel are first extracted from "the region that corresponds to a mismatch", and the pixels that correspond to the blood vessel are sequentially extracted from upstream or downstream of the blood vessel by using the extracted pixel as a starting point. Thus, as a result of changing the processing detail for extracting pixels that correspond to a blood vessel, it is sometimes possible to newly extract a blood vessel or stenosis that is not extracted when the position of a seed point is in the "proximal area".

Furthermore, by changing the threshold from "300" to "150", pixels that are not determined to be a blood vessel when the threshold is "300" may be determined to be a blood vessel so that a blood vessel or stenosis that is not previously detected may be newly extracted. Furthermore, by changing the threshold from a small value to a large value, pixels that are mistakenly determined to be a blood vessel when the threshold is a small value may be sometimes prevented from being determined to be a blood vessel. Although an explanation is given of a case where re-extraction is conducted after both the position of a seed point and the threshold are changed, there may be a case where re-extraction is conducted after any one of the position of a seed point and the threshold is changed.

Furthermore, when there is a stenosis in a blood vessel, the blood vessel is sometimes extracted discontinuously. For example, the calculation function 344 first extracts a blood vessel by using a position a1 illustrated in FIG. 6 as a seed point. Thus, the calculation function 344 extracts a blood vessel from the position a1 to a position a2 in FIG. 6. Furthermore, after the detection function 346 detects a mismatch, the correction function 349 re-extracts a blood vessel from CT image data by using a position b1, a position b2, a position b3, and a position b4, included in "the region that corresponds to the mismatch" as seed points. Specifically, the correction function 349 searches for a blood vessel in an arrow direction by using the position b1 as a seed point, searches for a blood vessel in an arrow direction by using the position b2 as a seed point, searches for a blood vessel in an arrow direction by using the position b3 as a seed point, and searches for a blood vessel in an arrow direction by using the position b4 as a seed point. Here, for example, the correction function 349 searches for a blood vessel by using the position b2 as a seed point, thereby re-extracting a blood vessel from a position a3 to a position a4 in FIG. 6. Then, the correction function 349 corrects a blood vessel region in the CT image data in accordance with the re-extracted blood vessel. For example, in accordance with a result of re-extraction, the correction function 349 adds a blood vessel region or corrects the shape of a blood vessel region. Here, FIG. 6 is a diagram that illustrates a blood vessel re-extraction process according to the first embodiment.

Here, although the blood vessel (the blood vessel from the position a3 to the position a4), which is re-extracted by the correction function 349, is extracted by being disconnected from any of the RCA, the LAD, and the LCX, it is sometimes related to a different blood vessel. For example, the blood vessel from the position a3 to the position a4 is sometimes part of the RCA, the LAD, or the LCX. Therefore, the correction function 349 determines a blood vessel that is related to the re-extracted blood vessel.

Figure 6:
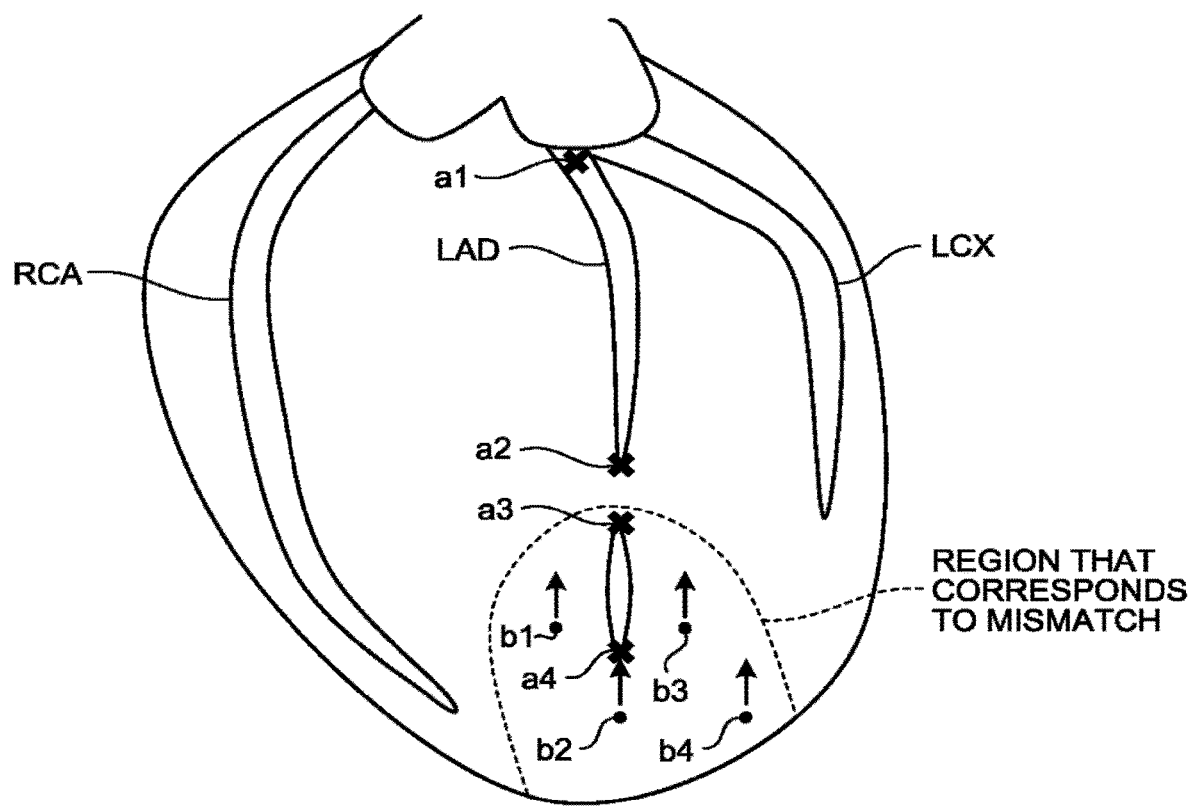
FIG. 6 is a diagram that illustrates a blood vessel re-extraction process according to the first embodiment.

For example, the correction function 349 first connects the core line of the blood vessel from the position a3 to the position a4 and the core line of the LAD illustrated in FIG. 6 with a curved line. Here, the correction function 349 connects the core line of the blood vessel from the position a3 to the position a4 and the core line of the LAD such that the curved line has the minimum curvature. In the same manner, the correction function 349 connects the core line of the blood vessel from the position a3 to the position a4 and the core line of the RCA illustrated in FIG. 6 with a curved line. In the same manner, the correction function 349 connects the core line of the blood vessel from the position a3 to the position a4 and the core line of the LCX illustrated in FIG. 6 with a curved line. Then, among the LAD, the RCA, and the LCX, the correction function 349 determines a blood vessel that is connectable by using a curved line with the minimum curvature as a blood vessel related to the blood vessel from the position a3 to the position a4. In other words, the correction function 349 determines a blood vessel related to the re-extracted blood vessel based on the curvature of curved line connecting the core lines.

For another example, the correction function 349 first connects the core line of the blood vessel from the position a3 to the position a4 and the core line of the LAD illustrated in FIG. 6 with a straight line. In the same manner, the correction function 349 connects the core line of the blood vessel from the position a3 to the position a4 and the core line of the RCA illustrated in FIG. 6 with a straight line. In the same manner, the correction function 349 connects the core line of the blood vessel from the position a3 to the position a4 and the core line of the LCX illustrated in FIG. 6 with a straight line. Then, among the LAD, the RCA, and the LCX, the correction function 349 determines a blood vessel that is connectable by using a shortest straight line as a blood vessel related to the blood vessel from the position a3 to the position a4. In other words, the correction function 349 determines a blood vessel related to the re-extracted blood vessel based on the distance between the core lines. Furthermore, the correction function 349 may determine a blood vessel related to the re-extracted blood vessel based on the curvature of curved line connecting the core lines and the distance between the core lines.

In the case illustrated in FIG. 6, the distance between the core line of the blood vessel from the position a3 to the position a4 and the core line of the LAD is short, and connectable by using an approximately straight line. Therefore, in the case illustrated in FIG. 6, the correction function 349 determines the LAD as a blood vessel related to the blood vessel from the position a3 to the position a4. In other words, the correction function 349 determines that the blood vessel from the position a3 to the position a4 is part of the LAD.

Figure 7:
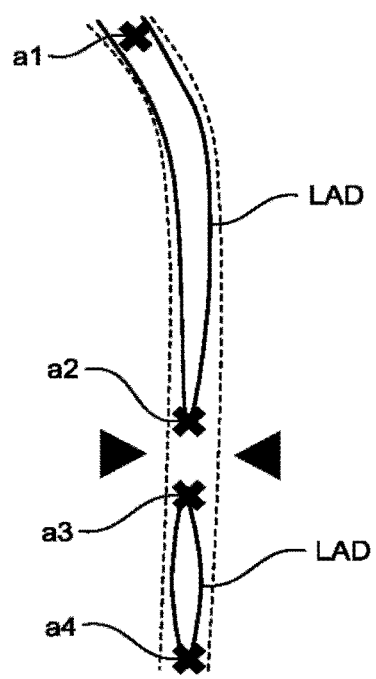
FIG. 7 is a diagram that illustrates an example of display of a blood vessel that is re-extracted according to the first embodiment.

Here, the display control function 348 may display a result of a re-extraction process by the correction function 349. For example, as illustrated in FIG. 7, the display control function 348 displays the blood vessel from the position a1 to the position a2 and the blood vessel from the position a3 to the position a4 as the LAD. Furthermore, the display control function 348 uses two triangles to display that there is a stenosis between the position a2 and the position a3. Furthermore, the display control function 348 uses dotted lines to display that the blood vessel from the position a1 to the position a2 and the blood vessel from the position a3 to the position a4 are a continuous blood vessel. Here, FIG. 7 is a diagram that illustrates an example of display of a blood vessel that is re-extracted according to the first embodiment.

Here, the display of FIG. 7 is an example, and various modifications are possible. For example, instead of the dotted lines in FIG. 7, the display control function 348 may display the line connecting the position a1, the position a2, the position a3, and the position a4. That is, the display control function 348 may use a continuous line to display the core line of the LAD including a stenosis.

Furthermore, with reference to FIG. 6, an explanation has been given of a case where a blood vessel is re-extracted from CT image data by using multiple points (the position b1, the position b2, the position b3, and the position b4) included in "the region that corresponds to the mismatch" as seed points. However, this is not a limitation on embodiments. For example, the correction function 349 re-extracts a blood vessel from CT image data by using a single point included in "the region that corresponds to the mismatch" as a seed point. Here, if a blood vessel is not newly extracted from "the region that corresponds to the mismatch", the correction function 349 changes the position of the seed point in "the region that corresponds to the mismatch" and re-extracts a blood vessel from the CT image data. Conversely, if a blood vessel is newly extracted from "the region that corresponds to the mismatch", the correction function 349 terminates the re-extraction process.

After the correction function 349 corrects CT image data, the calculation function 344 re-calculates the first function index on the basis of a blood vessel region in the corrected CT image data. For example, the calculation function 344 conducts fluid analysis on the basis of a blood vessel region in the corrected CT image data and calculates FFR at each position of the blood vessel region. Then, the image generation function 342 generates CT image data (FFR image data) that represents FFR of the blood vessel region. Then, the calculation function 344 determines a blood vessel region that dominates each position of the FFR image data and re-calculates FFR of the determined blood vessel region as the first function index.

Then, the detection function 346 re-acquires morphological information about the heart of the subject from FFR image data. For example, the detection function 346 determines an ischemic region based on the re-calculated first function index in CT image data. Specifically, the detection function 346 determines whether the value of FFR, which is re-calculated as the first function index, is equal to or less than the threshold with regard to each position of the heart in FFR image data, and it determines the set of positions where the value of FFR is equal to or less than the threshold as an ischemic region. Furthermore, the detection function 346 calculates the quantity of myocardium in which ischemia occurs on the basis of the ischemic region. Furthermore, the display control function 348 displays an FFR image indicating an ischemic region or an ischemic myocardium quantity on the display 320.

Figure 8:
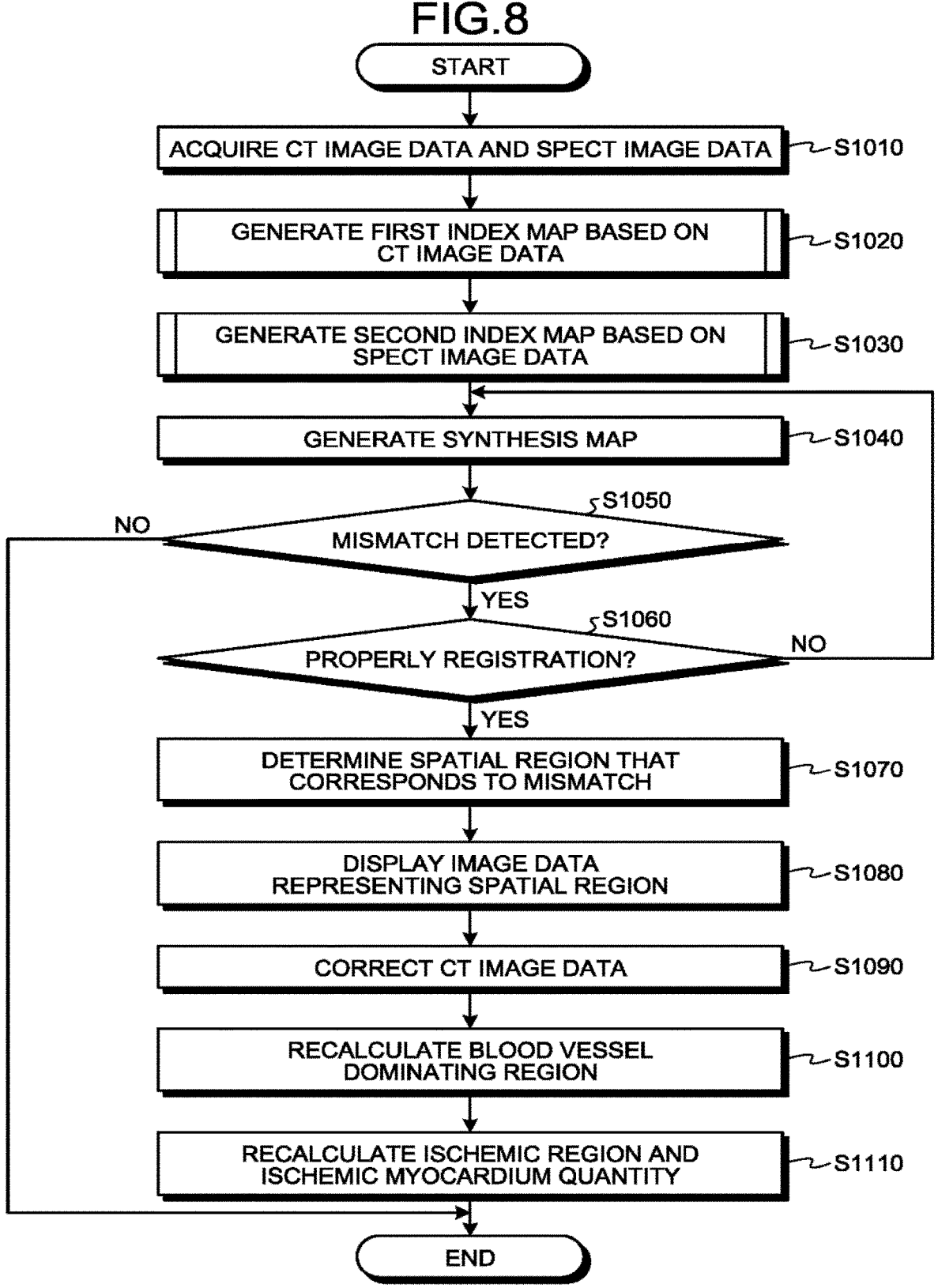
FIG. 8 is a flowchart that illustrates a sequential flow of the process of an image processing apparatus according to the first embodiment.

Next, with reference to FIG. 8, an example of steps of a process performed by the image processing apparatus 300 is explained. FIG. 8 is a flowchart that illustrates a sequential flow of the process of the image processing apparatus 300 according to the first embodiment. In FIG. 8, Step S1040 is a step that corresponds to the image generation function 342. Step S1010 is a step that corresponds to the acquisition function 343. Step S1050, Step S1100, and Step S1110 are steps that correspond to the detection function 346. Step S1070 is a step that corresponds to the determination function 347. Step S1060 and Step S1080 are steps that correspond to the display control function 348. Step S1090 is a step that corresponds to the correction function 349.

First, the processing circuitry 340 acquires CT image data acquired by an X-ray CT apparatus and SPECT image data acquired by a SPECT apparatus (Step S1010). Next, the processing circuitry 340 generates the first index map based on the CT image data (Step S1020) and generates the second index map based on the SPECT image data (Step S1030). Here, Step S1020 and Step S1030 are in any order, and they may be simultaneously conducted. The flow of the process at Step S1020 and the flow of the process at Step S1030 are described later.

Next, the processing circuitry 340 registers and synthesizes the first index map and the second index map to generate a synthesis map (Step S1040) and determines whether a mismatch between the first index map and the second index map has been detected from the synthesis map (Step S1050). When a mismatch has been detected (Yes at Step S1050), the processing circuitry 340 determines whether the registration between the first index map and the second index map have been proper in accordance with an operation, or the like, from the operator who has viewed the synthesis map (Step S1060). When it is determined that the registration have not been proper (No at Step S1060), the processing circuitry 340 proceeds to Step S1040 again.

Conversely, when it is determined that the registration have been proper (Yes at Step S1060), the processing circuitry 340 determines a spatial region that corresponds to the mismatch in the CT image data (Step S1070). Then, the processing circuitry 340 displays image data such as CT image data representing the spatial region that corresponds to the mismatch on the display 320 (Step S1080). Furthermore, the processing circuitry 340 corrects the CT image data in accordance with the mismatch (Step S1090). Then, the processing circuitry 340 re-calculates a blood vessel dominating region on the basis of the corrected CT image data (Step S1100) and re-acquires the first function index. Then, after the processing circuitry 340 re-calculates an ischemic range and an ischemic myocardium quantity on the basis of the re-acquired first function index (Step S1110) or when no mismatch is detected at Step S1050, the process is terminated.

Figure 9:
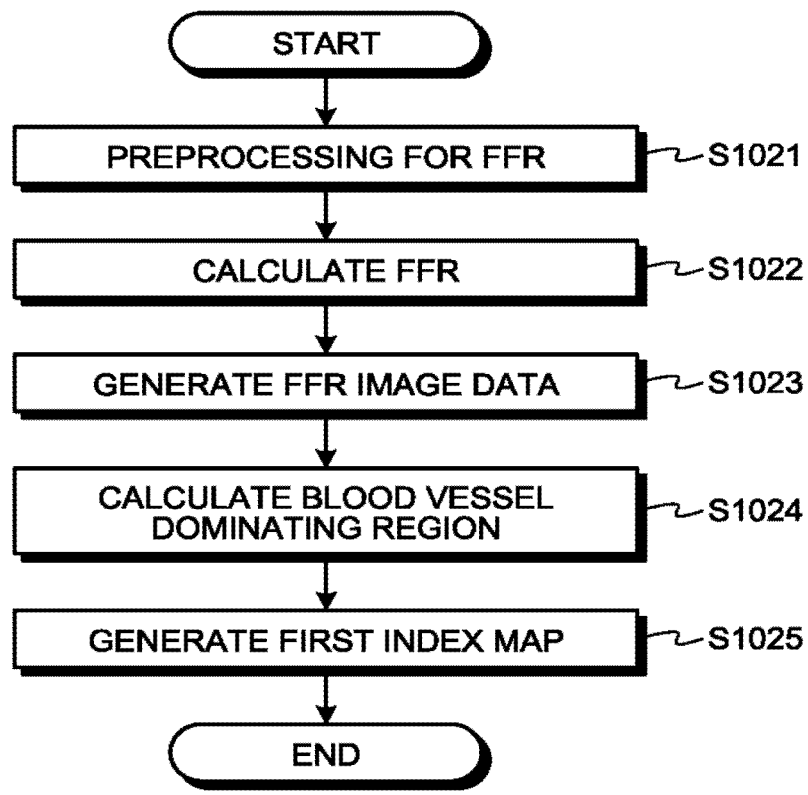
FIG. 9 is a flowchart that illustrates a sequential flow of the process to generate the first index map according to the first embodiment.

Next, with reference to FIG. 9, generation of the first index map according to the first embodiment is explained. FIG. 9 is a flowchart that illustrates a sequential flow of the process to generate the first index map according to the first embodiment. Here, FIG. 9 illustrates the process that corresponds to Step S1020 in FIG. 8. In FIG. 9, Step S1023 and Step S1025 are steps that correspond to the image generation function 342. Step S1021, Step S1022, and Step S1024 are steps that correspond to the calculation function 344.

First, the processing circuitry 340 uses the CT image data acquired at Step S1010 of FIG. 8 to perform preprocessing for calculating FFR (Step S1021). For example, as preprocessing for FFR, the processing circuitry 340 determines a blood vessel region in CT image data and acquires blood vessel form data. Then, the processing circuitry 340 conducts fluid analysis by using a blood vessel region in CT image data as an analysis model to calculate FFR with respect to each position of the blood vessel region (Step S1022).

Next, the processing circuitry 340 generates FFR image data from CT image data including morphology information on the coronary artery and the FFR calculated from the CT image data (Step S1023). Then, the processing circuitry 340 calculates a blood vessel dominating region in accordance with a blood vessel region in the FFR image data (Step S1024) and calculates the first function index. Then, the processing circuitry 340 projects the first function index onto a plane, thereby generating the first index map (Step S1025).

Figure 10:
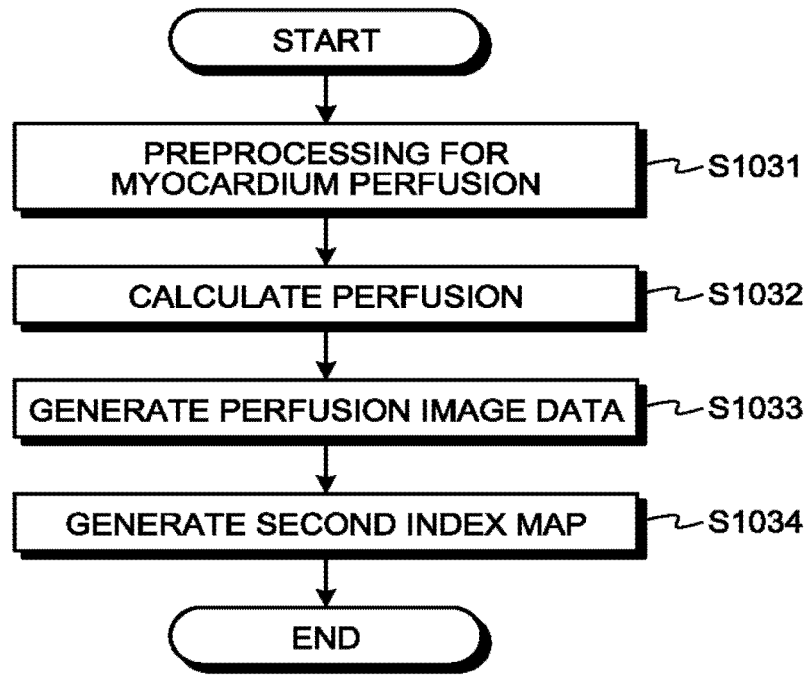
FIG. 10 is a flowchart that illustrates a sequential flow of the process to generate the second index map according to the first embodiment.

Next, with reference to FIG. 10, an explanation is given of generation of the second index map according to the first embodiment. FIG. 10 is a flowchart that illustrates a sequential flow of the process to generate the second index map according to the first embodiment. Here, FIG. 10 illustrates the process that corresponds to Step 1030 of FIG. 8. In FIG. 10, Step S1033 and Step S1034 are steps that correspond to the image generation function 342. Step S1031 and Step S1032 are steps that correspond to the index acquisition function 345.

First, the processing circuitry 340 performs preprocessing for calculating myocardium perfusion by using the SPECT image data acquired at Step S1010 of FIG. 8 (Step S1031). For example, as preprocessing for myocardium perfusion, the processing circuitry 340 performs a process to generate a TDC based on comparison between multiple sets of SPECT image data. Then, the processing circuitry 340 calculates perfusion (Step S1032) and acquires the second function index with respect to each position of the heart. For example, as the second function index, the processing circuitry 340 acquires the maximum value of density obtained from a TDC, a blood flow, or the like.

Next, the processing circuitry 340 generates perfusion image data indicating the distribution of second function indexes on the basis of the SPECT image data and a calculation result of perfusion (Step S1033). Then, the processing circuitry 340 projects the second function index in the perfusion image data onto a plane, thereby generating the second index map (Step S1034).

As described above, according to the first embodiment, the acquisition function 343 acquires CT image data and SPECT image data including the heart of the subject. The calculation function 344 extracts a blood vessel region that corresponds to a blood vessel included in CT image data, calculates FFR in the blood vessel region and, based on the FFR, calculates the first function index as an index indicating a function of the tissue to which nutrients are supplied from the blood vessel. The index acquisition function 345 acquires, on the basis of SPECT image data, the second function index as an index indicating a function of the tissue to which nutrients are supplied from a blood vessel. The detection function 346 detects a mismatch between the first function index and the second function index. The determination function 347 determines a spatial region that corresponds to a mismatch in the heart of the subject.

Therefore, the image processing apparatus 300 according to the first embodiment uses SPECT image data to evaluate morphological information such as an ischemic range obtained from a blood vessel region in CT image data, whereby the accuracy of morphological information may be improved. For example, when a mismatch is detected, the image processing apparatus 300 is capable of taking various measures to eliminate the mismatch, such as correction of CT image data, and when no mismatch is detected, the reliability of morphological information may be improved.

Furthermore, according to the first embodiment, the correction function 349 corrects CT image data in accordance with a mismatch. Therefore, the image processing apparatus 300 according to the first embodiment is capable of acquiring morphological information such as ischemic regions or ischemic myocardium quantities more accurately on the basis of a higher-accuracy blood vessel region including information from SPECT image data and providing information useful for considering treatment strategies or measuring treatment effects.

Furthermore, according to the first embodiment, the correction function 349 re-extracts a blood vessel from the heart region that is determined to be an ischemic region based on CT image data and that is determined not to be an ischemic region based on SPECT image data. Therefore, the image processing apparatus 300 according to the first embodiment may prevent blood vessels from being missed at the stage of determining blood vessel regions and prevent unnecessary treatment for regions where ischemia does not occur.

Furthermore, according to the first embodiment, the correction function 349 re-extracts a blood vessel from the heart region that is determined to be an ischemic region based on SPECT image data and that is determined not to be an ischemic region based on CT image data. Therefore, the image processing apparatus 300 according to the first embodiment makes it possible to prevent responsible stenosis from being missed and to make proper treatment plans based on more accurate morphological information.

Furthermore, according to the first embodiment, the display control function 348 displays image data on the heart of the subject indicating a spatial region that corresponds to a mismatch on the display 320. Therefore, the image processing apparatus 300 according to the first embodiment allows operators to determine whether the heart region that corresponds to a mismatch is an ischemic region and, when it is difficult to determine whether it is an ischemic region, corrects CT image data, or the like, to improve the accuracy of morphological information.

In the above-described first embodiment, an explanation is given of a case where the first function index and the second function index are projected onto a plane to generate the first index map and the second index map and a mismatch is detected from a synthesis map that is a synthesis of the first index map and the second index map. In a second embodiment, an explanation is given of a case where the first function index and the second function index are compared without being projected onto a plane and a mismatch is detected from volume data such as CT image data or SPECT image data.

The image processing apparatus 300 according to the second embodiment has the same configuration as that of the image processing apparatus 300 illustrated in FIG. 1, and there is a difference in part of processing by the image generation function 342, the calculation function 344, the index acquisition function 345, the detection function 346, and the determination function 347. Therefore, the part having the same configuration as that described in the first embodiment is attached with the same reference numeral in FIG. 1, and explanation is omitted.

First, based on FFR image data, the calculation function 344 calculates the first function index as an index indicating a function of the tissue to which nutrients are supplied from a blood vessel with respect to each position of the heart of the subject. Furthermore, based on SPECT image data, the index acquisition function 345 calculates the second function index as an index indicating a function of the tissue to which nutrients are supplied from a blood vessel with respect to each position of the heart of the subject. Furthermore, the image generation function 342 generates perfusion image data indicating the distribution of the second function indexes.

Furthermore, the detection function 346 determines an ischemic region in FFR image data. For example, the detection function 346 determines whether the first function index (the value of FFR) is equal to or less than the threshold with respect to each position of the heart included in FFR image data and determines the set of positions where the value of FFR is equal to or less than the threshold as an ischemic region. Furthermore, the detection function 346 determines an ischemic region in perfusion image data. For example, the detection function 346 determines whether the second function index (e.g., a blood flow) is equal to or less than the threshold with respect to each position of the heart included in perfusion image data and determines the set of positions where a blood flow is equal to or less than the threshold as an ischemic region.

Furthermore, the image generation function 342 registers FFR image data indicating the distribution of the first function indexes and perfusion image data indicating the distribution of the second function indexes. For example, the image generation function 342 extracts a feature point from each of the FFR image data and the perfusion image data and registers the FFR image data and the perfusion image data such that the positions of feature points are matched.

Then, the detection function 346 detects a mismatch between the first function index and the second function index from FFR image data or perfusion image data. For example, the detection function 346 detects the subject's heart region that is an ischemic region in FFR image data and that is not an ischemic region in perfusion image data as a mismatch. Furthermore, for example, the detection function 346 detects the subject's heart region that is an ischemic region in perfusion image data and that is not an ischemic region in FFR image data as a mismatch. Then, the determination function 347 determines a spatial region that corresponds to a mismatch in volume data such as FFR image data or perfusion image data.

Although an explanation is given of a case where a mismatch is detected by comparing FFR image data and perfusion image data, this is not a limitation on embodiments. For example, the image generation function 342 first generates a three-dimensional map by extracting only the distribution of the first function indexes from FFR image data and generates a three-dimensional map by extracting only the distribution of the second function indexes from perfusion image data. Then, the detection function 346 compares the generated three-dimensional maps, thereby detecting a mismatch.

As described above, according to the second embodiment, the image processing apparatus 300 detects a mismatch by comparing the first function index and the second function index in volume data (three-dimensional function index map). Therefore, with the image processing apparatus 300 according to the second embodiment, the accuracy of morphological information may be improved without generating a polar map. That is, the image processing apparatus 300 according to the second embodiment is applicable to examination of various sites such as brain or liver as well as heart.

Although the first and the second embodiments are explained above, various different embodiments may be implemented other than the above-described embodiments.

In the above-described embodiment, an explanation is given of a case where a dominant blood vessel is determined with respect to each position of a site of the subject in FFR image data and FFR of the determined dominant blood vessel is acquired as the first function index; however, this is not a limitation on embodiments.

For example, there may be a case where the calculation function 344 calculates the first function index by using a dynamic fluid index within a blood vessel or a fluid index regarding the flow rate of blood instead of FFR or together with FFR. That is, the calculation function 344 is capable of calculating the first function index on the basis of not only FFR but also various fluid indexes. Dynamic fluid indexes within blood vessels include, for example, a pressure, a vector, or shear stress. Fluid indexes regarding the flow rate of blood include, for example, a flow rate or a flow velocity.

Furthermore, for example, there may be a case where the calculation function 344 determines a dominant blood vessel with respect to each position of CT image data and acquires the value indicating the blood vessel thickness of the determined dominant blood vessel as the first function index. That is, as the fluid index, the calculation function 344 may use the value indicating the thickness of a blood vessel. For example, the detection function 346 is capable of acquiring a coronary artery wall outline from morphology information on a blood vessel region in CT image data and acquiring a coronary-artery wall outline cross-sectional area as the value indicating the thickness of a blood vessel. Furthermore, for example, the detection function 346 is capable of acquiring the diameter or circumference of a coronary artery based on a coronary artery wall outline as the value indicating the thickness of a blood vessel. Furthermore, the region dominated by a thick blood vessel is often not an ischemic region, and the region dominated by a thin blood vessel is often an ischemic region. Therefore, the detection function 346 is capable of determining, as an ischemic region, a region of which the value indicating the thickness of a blood vessel, acquired as the first function index, is smaller than a threshold. Furthermore, when the value indicating the thickness of a dominant blood vessel is acquired as the first function index, the calculation function 344 is capable of acquiring the first function index from CT image data where FFR of a blood vessel region is not represented. That is, when the thickness of a dominant blood vessel is acquired as the first function index, there may be a case where FFR analysis and FFR image data generation are not conducted.

Furthermore, in the above-described embodiment, an explanation is given of a case where a dominant blood vessel is determined based on only the distance between each position of a site of the subject and a blood vessel region. However, this is not a limitation on embodiments. For example, there may be a case where the calculation function 344 determines a dominant blood vessel in accordance with a weighted distance. Here, the weight is, for example, FFR or the thickness of a blood vessel.

For example, the calculation function 344 first expands a blood vessel region in accordance with the value of FFR or the thickness of a blood vessel (for example, a diameter is increased in proportion to FFR). Then, with respect to each position of a site of the subject, the calculation function 344 determines a blood vessel region with the minimum distance to an edge (outline) of the expanded blood vessel region as a dominant blood vessel. That is, the calculation function 344 determines a dominant blood vessel in accordance with not the distance to the core line of a blood vessel region but the distance (weighted distance) to the region expanded in accordance with FFR. Thus, a wider dominating region of a blood vessel with a high nutritional capability is calculated, and morphological information on ischemic regions, or the like, may be calculated more accurately.

Furthermore, for example, with regard to the position 21 of a site of the subject, the calculation function 344 first acquires the distance between the position P1 and each position of a blood vessel region. Then, with respect to each position of the blood vessel region, the calculation function 344 calculates the value based on the value of FFR or the thickness of a blood vessel and the distance to the position P1 as a weighted distance. For example, with respect to each position of a blood vessel region, the calculation function 344 calculates a value as a weighted distance by dividing the distance to the position P1 by a coronary-artery wall outline cross-sectional area. Then, the calculation function 344 determines a blood vessel region with the minimum weighted distance as a dominant blood vessel at the position P1. Furthermore, the calculation function 344 determines a dominant blood vessel with regard to positions other than the position P1 in the same manner. Thus, a wider dominating region of a blood vessel with a high nutritional capability is calculated, and morphological information on ischemic regions may be calculated more accurately.

Furthermore, CT image data according to the above-described embodiment is an example of morphology image data, and the same image processing is also possible by using different morphology image data instead of CT image data. For example, the calculation function 344 is capable of calculating the first function index on the basis of MR image data. Furthermore, for example, the calculation function 344 is capable of calculating the first function index on the basis of various types of CT image data (e.g., FFR image data) representing a spatial distribution of fluid indexes. That is, the calculation function 344 is capable of calculating the first function index on the basis of any morphology image data with which blood vessel form data may be acquired.

Furthermore, SPECT image data according to the above-described embodiment is an example of function image data, and the same image processing is possible by using different function image data instead of SPECT image data. For example, the index acquisition function 345 is capable of acquiring the second function index in accordance with PET image data, CT perfusion image data, or MR perfusion image data.

Furthermore, for example, the index acquisition function 345 is capable of acquiring the second function index on the basis of image data representing a result of heart function analysis on CT image data, image data representing a result of heart function analysis on MR image data, or image data representing a result of heart function analysis on ultrasound image data. For example, the index acquisition function 345 acquires, as the second function index, an analysis result of the heart function, such as time changes in the left ventricle volume within one heartbeat, from MR image data by electrocardiogram synchronization imaging. Then, the index acquisition function 345 compares the second function index and the model data (a result of heart function analysis with regard to the heart where ischemia does not occur, or the like), thereby determining ischemic regions.

Furthermore, in the above-described embodiment, an explanation is given of a case where the first function index based on morphology image data is compared with the second function index based on function image data to detect a mismatch. However, this is not a limitation on embodiments. For example, the detection function 346 may compare a blood vessel region extracted from morphology image data with the second function index based on function image data to detect a mismatch.

For example, the acquisition function 343 acquires CT image data and SPECT image data including the heart of the subject. Next, the calculation function 344 extracts a blood vessel region that corresponds to the blood vessel included in the CT image data acquired by the acquisition function 343. Furthermore, on the basis of the SPECT image data, the index acquisition function 345 acquires the second function index that indicates the function of the tissue to which nutrients are supplied from the blood vessel.

Next, the detection function 346 compares the blood vessel region with the second function index to detect a mismatch. For example, the detection function 346 first acquires the length of each blood vessel of the subject on the basis of the extracted blood vessel region. For example, the detection function 346 acquires the length of each of the RCA, the LAD, and the LCX of the subject.

Furthermore, the detection function 346 acquires the reference value of a length with respect to each of the RCA, the LAD, and the LCX. That is, the detection function 346 acquires a typical length of each blood vessel. The reference value is previously stored in the memory 330. For example, the detection function 346 acquires the length of each blood vessel with regard to multiple patients. Next, the detection function 346 classifies the acquired length of a blood vessel by patient information (personality, physical size, or the like). Then, the detection function 346 stores the average value, the middle value, or the like, of the acquired length of a blood vessel as the reference value of a length in the memory 330. Then, after the acquisition function 343 acquires CT image data, the detection function 346 acquires the reference value of the length of each blood vessel from the memory 330 in accordance with patient information on the subject. That is, the detection function 346 selects an appropriate reference value in consideration of individual differences in the length of a blood vessel.

Figure 11:
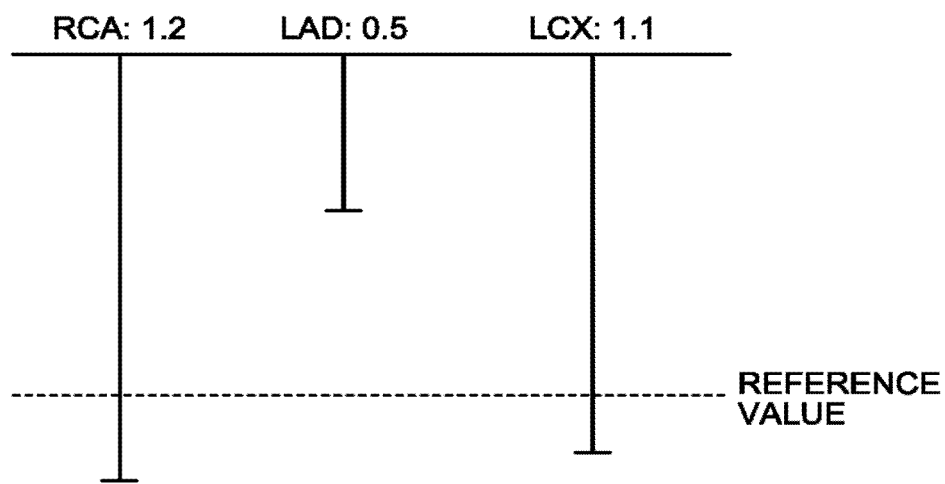
FIG. 11 is a diagram that illustrates detection of a mismatch region according to a third embodiment.

Then, the detection function 346 calculates the rate of the length of each blood vessel of the subject with respect to the acquired reference value. For example, as illustrated in FIG. 11, the detection function 346 calculates "1.2" as the rate of the length of the RCA based on CT image data on the subject with respect to the reference value of the length of the RCA. Furthermore, the detection function 346 calculates "0.5" as the rate of the length of the LAD based on CT image data on the subject with respect to the reference value of the length of the LAD. Moreover, the detection function 346 calculates "1.1" as the rate of the length of the LCX based on CT image data on the subject with respect to the reference value of the length of the LCX. Here, FIG. 11 is a diagram that illustrates detection of a mismatch region according to a third embodiment.

In the case illustrated in FIG. 11, the rate of the RCA and the LCX of the subject with respect to the reference value is a value close to "1". That is, the RCA and the LCX of the subject have a typical length. Furthermore, the rate of the LAD of the subject with respect to the reference value is "0.5". That is, the length of the LAD of the subject is approximately half the typical length. Therefore, the blood vessel region extracted from CT image data indicates that there is a possibility of ischemia occurring in the tissue to which nutrients are supplied from the LAD. Here, the second function index sometimes indicates that ischemia does not occur in the tissue to which nutrients are supplied from the LAD. In this case, the detection function 346 detects the tissue to which nutrients are supplied from the LAD as a mismatch. That is, the detection function 346 detects, as a mismatch, the region of which a blood vessel region based on CT image data indicates that it is an ischemic region and the second function index based on SPECT image data indicates that it is not an ischemic region.

Furthermore, in some cases, the second function index indicates that ischemia occurs although the length of each blood vessel of the subject is nearly equal to the reference value. In this case, the detection function 346 detects, as a mismatch, the region of which a blood vessel region based on CT image data indicates that it is not an ischemic region and the second function index based on SPECT image data indicates that it is an ischemic region. For example, the detection function 346 detects, as a mismatch, a blood vessel region based on CT image data and a region included with a predetermined distance from the blood vessel region among the regions indicated as ischemic regions by the second function index.

As described above, the detection function 346 detects a mismatch between a blood vessel region extracted from CT image data and the second function index based on SPECT image data. That is, the detection function 346 is capable of detecting a mismatch without using the fluid index or the first function index based on CT image data.

An explanation is given above of a case where the length of each blood vessel of the subject is acquired from a blood vessel region extracted from CT image data and a mismatch with the second function index is detected based on the rate of the length of each blood vessel of the subject with respect to the reference value. However, this is not a limitation on embodiments. For example, the detection function 346 may detect a mismatch with the second function index in accordance with a result of mutual comparison of the length of each blood vessel of the subject. For example, when the length of the LAD in the blood vessel region extracted from CT image data is significantly short as compared with other blood vessels, and the second function index indicates that ischemia does not occur in the tissue to which nutrients are supplied from the LAD, the detection function 346 detects the tissue to which nutrients are supplied from the LAD as a mismatch.

Furthermore, in the above-described embodiment, an explanation is given by using the image processing apparatus 300 as an example. That is, an explanation is given of a case where the image processing apparatus 300 acquires morphology image data acquired by an X-ray CT apparatus and function image data acquired by an SPECT apparatus and performs each of the above-described processes. However, this is not a limitation on embodiments. For example, there may be a case where an X-ray CT apparatus uses acquired morphology image data and function image data acquired from an SPECT apparatus and performs each of the above-described processes. Furthermore, for example, there may be a case where an SPECT apparatus uses acquired function image data and morphology image data acquired from an X-ray CT apparatus and performs each of the above-described processes. In other words, the above-described image processing is possible by any medical-image diagnostic apparatus and any image processing apparatus capable of acquiring morphology image data and function image data.

Components of each apparatus according to the first to the third embodiments are functionally conceptual, and they do not necessarily need to be physically configured as illustrated in the drawings. Specifically, specific forms of separation and combination of each apparatus are not limited to those depicted in the drawings, and a configuration may be such that all or some of them are functionally or physically separated or combined in an arbitrary unit depending on various types of loads, usage, or the like. Furthermore, all or any of various processing functions performed by each apparatus may be implemented by a CPU or a program analyzed and executed by the CPU or by wired logic hardware.

The image processing method described in the first to the third embodiments may be performed when a prepared image processing program is performed by a computer such as a personal computer or workstation. The image processing program is recorded in a computer-readable storage medium, such as hard disk, flexible disk (FD), CD-ROM, MO, or DVD, and it is also executable when it is read from a recording medium by a computer. Further, the programs may be provided or distributed by being stored on a computer connected to a network, such as the Internet, and being downloaded via the network. For example, these programs are configured as modules including the above described function. As to actual hardware, by a CPU reading and executing the programs from a storage medium, such as a ROM, the modules are loaded on the main storage, and generated on the main storage.

According to at least one of the above-described embodiments, the accuracy of morphological information may be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising processing circuitry configured to
   acquire morphology image data including a site of a subject and function image data including the site,
   extract a blood vessel region that corresponds to a blood vessel included in the morphology image data, calculate a fluid index in the blood vessel region, and based on the fluid index, calculate a first function index as an index indicating a function of a tissue to which a nutrient is supplied from the blood vessel,
   acquire a second function index as an index indicating a function of the tissue based on the function image data,
   detect a mismatch between the first function index and the second function index, and
   determine a spatial region that corresponds to the mismatch in the site.

2. The image processing apparatus according to claim 1, wherein the processing circuitry is configured to
   determine, as the spatial region, a region that corresponds to the mismatch in the morphology image data, and
   display image data on the site indicating the spatial region on a display.

3. The image processing apparatus according to claim 1, wherein
   the site is a heart of the subject, and
   the first function index and the second function index are function indexes of myocardium.

4. The image processing apparatus according to claim 3, wherein the processing circuitry is further configured to
   generate a first index map by projecting the first function index onto a plane, generate a second index map by projecting the second function index onto a plane, and generate a synthesis map by registering and synthesizing the first index map and the second index map, and as the mismatch, detect a mismatch between the first index map and the second index map from the synthesis map.

5. The image processing apparatus according to claim 4, wherein
   the first function index and the second function index are function indexes regarding ischemia of the site, and
   the processing circuitry is configured to determine an ischemic region indicating ischemia of the site in each of the first index map and the second index map and detect, as the mismatch from the synthesis map, at least any one of a region that is an ischemic region in the first index map and that is not an ischemic region in the second index map and a region that is an ischemic region in the second index map and that is not an ischemic region in the first index map.

6. The image processing apparatus according to claim 1, wherein
   the first function index and the second function index are function indexes regarding ischemia of the site, and
   the processing circuitry is configured to determine an ischemic region based on the first function index in the morphology image data, determine an ischemic region based on the second function index in the function image data, and detect, as the mismatch from the morphology image data or the function image data, at least any one of a region of the site that is an ischemic region in the morphology image data and that is not an ischemic region in the function image data and a region of the site that is an ischemic region in the function image data and that is not an ischemic region in the morphology image data.

7. The image processing apparatus according to claim 1, wherein the processing circuitry is further configured to correct the morphology image data in accordance with the mismatch.

8. The image processing apparatus according to claim 7, wherein the processing circuitry is configured to re-extract a blood vessel from the morphology image data by using a parameter different from an extraction parameter used to extract the blood vessel region and correct the blood vessel region in accordance with the re-extracted blood vessel.

9. The image processing apparatus according to claim 8, wherein
   the processing circuitry is configured to
   as the spatial region, determine a region that corresponds to the mismatch in the morphology image data, and
   re-extract a blood vessel from the morphology image data by using one or more points included in the determined region as seed points and correct the blood vessel region in accordance with the re-extracted blood vessel.

10. The image processing apparatus according to claim 9, wherein the processing circuitry is configured to determine a blood vessel related to the re-extracted blood vessel.

11. The image processing apparatus according to claim 8, wherein
    the processing circuitry is configured to
    compare a pixel value of each pixel of the morphology image data with a threshold, thereby extracting the blood vessel region, and
    re-extract a blood vessel from the morphology image data by using a different threshold and correct the blood vessel region in accordance with the re-extracted blood vessel.

12. The image processing apparatus according to claim 7, wherein the processing circuitry is configured to
    re-calculate the first function index based on the corrected blood vessel region, and
    determine an ischemic region based on the re-calculated first function index in the morphology image data.

13. The image processing apparatus according to claim 12, wherein the processing circuitry is configured to conduct fluid analysis based on the corrected blood vessel region and re-calculate the first function index by using a result of the fluid analysis.

14. The image processing apparatus according to claim 1, wherein
the morphology image data is CT (computed tomography) image data, CT image data representing a spatial distribution of the fluid index, or MR (magnetic resonance) image data, and
the function image data is SPECT (single photon emission computed tomography) image data, PET (positron emission computed tomography) image data, CT perfusion image data, image data representing a result of heart function analysis with regard to CT image data, MR perfusion image data, image data representing a result of heart function analysis with regard to MR image data, or image data representing a result of heart function analysis with regard to ultrasound image data.

15. The image processing apparatus according to claim 1, wherein the processing circuitry is configured to determine, with respect to each position of the morphology image data, a blood vessel region that dominates the position and acquire, as the first function index, a value indicating fractional flow reserve in the determined blood vessel region.

16. The image processing apparatus according to claim 15, wherein the processing circuitry is configured to determine, with respect to each position of the morphology image data, a blood vessel region with a minimum distance from the position as a blood vessel region that dominates the position.

17. The image processing apparatus according to claim 1, wherein the processing circuitry is configured to determine, with respect to each position of the morphology image data, a blood vessel region that dominates the position and acquire, as the first function index, a value indicating a thickness of a blood vessel in the determined blood vessel region.

18. The image processing apparatus according to claim 15, wherein the processing circuitry is configured to determine, with respect to each position of the morphology image data, a blood vessel region with a minimum weighted distance as a blood vessel region that dominates the position, at least any one of a value indicating fractional flow reserve and a value indicating a thickness of a blood vessel being used as a weight for a distance from the position.

19. An image processing apparatus comprising processing circuitry configured to
acquire morphology image data including a site of a subject and function image data including the site,
extract a blood vessel region that corresponds to a blood vessel included in the morphology image data,
acquire a function index indicating a function of a tissue to which a nutrient is supplied from the blood vessel based on the function image data,
detect a mismatch between the blood vessel region and the function index, and
determine a spatial region that corresponds to the mismatch in the site.

20. An image processing method comprising:
acquiring morphology image data including a site of a subject and function image data including the site,
extracting a blood vessel region that corresponds to a blood vessel included in the morphology image data,
calculating a fluid index in the blood vessel region, and based on the fluid index, calculating a first function index as an index indicating a function of a tissue to which a nutrient is supplied from the blood vessel,
acquiring a second function index as an index indicating a function of the tissue based on the function image data,
detecting a mismatch between the first function index and the second function index, and
determining a spatial region that corresponds to the mismatch in the site.

* * * * *

UNITED STATES PATENT AND TRADEMARK OFFICE
CERTIFICATE OF CORRECTION

PATENT NO. : 10,565,709 B2
APPLICATION NO. : 16/006218
DATED : February 18, 2020
INVENTOR(S) : Kazumasa Arakita et al.

Page 1 of 1

It is certified that error appears in the above-identified patent and that said Letters Patent is hereby corrected as shown below:

On the Title Page

Item (73), should read:
-- Assignee: Canon Medical Systems Corporation, Otawara-shi (JP) --

Item (74), should read:
-- *Attorney, Agent, or Firm* --- Oblon, McClelland, Maier & Neustadt, L.L.P. --

Signed and Sealed this
Seventh Day of April, 2020

Andrei Iancu
*Director of the United States Patent and Trademark Office*